United States Patent [19]
Giungo

[11] Patent Number: 5,817,075
[45] Date of Patent: Oct. 6, 1998

[54] METHOD FOR PREPARATION AND TRANSPLANTATION OF PLANAR IMPLANTS AND SURGICAL INSTRUMENT THEREFOR

[75] Inventor: John Giungo, Norristown, Pa.

[73] Assignee: Photogenesis, Inc., Los Angeles, Calif.

[21] Appl. No.: 395,699

[22] Filed: Feb. 28, 1995

Related U.S. Application Data

[63] Continuation-in-part of Ser. No. 33,105, Mar. 16, 1993, abandoned, and a continuation-in-part of Ser. No. 322,735, Oct. 13, 1994, which is a continuation of Ser. No. 566,996, Aug. 13, 1990, abandoned, which is a continuation-in-part of Ser. No. 394,377, Aug. 14, 1989, abandoned.

[51] Int. Cl.$^6$ .................................................. A61M 35/00
[52] U.S. Cl. ............................ 604/294; 604/239; 604/59; 128/754; 606/107; 606/166; 623/5
[58] Field of Search ................................ 604/57, 59, 272, 604/294, 289, 290, 295, 239, 187; 128/753, 754, 763, 770; 606/167, 170, 171, 107, 166; 623/5

[56] References Cited

U.S. PATENT DOCUMENTS

| | | |
|---|---|---|
| 3,934,591 | 1/1976 | Gleason . |
| 4,014,342 | 3/1977 | Staub et al. . |
| 4,304,866 | 12/1981 | Green et al. ............................ 435/240 |

(List continued on next page.)

FOREIGN PATENT DOCUMENTS

| | | |
|---|---|---|
| 0 340 698 | 11/1989 | European Pat. Off. . |
| 0428998 | 5/1991 | European Pat. Off. . |
| 0 535 506 A1 | 4/1993 | European Pat. Off. . |
| 90 912685 | 2/1995 | European Pat. Off. . |
| 3632786 | 3/1988 | Germany . |
| 40 04 921 A1 | 8/1991 | Germany . |
| WO 91/02499 | 3/1991 | WIPO . |
| WO 92/08406 | 11/1991 | WIPO . |
| PCT/US96/02267 | 2/1996 | WIPO . |
| PCT/US96/02270 | 2/1996 | WIPO . |

OTHER PUBLICATIONS

Adolph; "Function and Structure in Isolated Subretinal Transplants", Invest. Ophthalmol. Vis. Sci. 34:1086, #4, abs. #1933–89, Mar. 15, 1993.

Anderson; "Retinal Detachment in the Cat; The Pigment Epithelial–Photoreceptor Interface", Invest. Ophthalmol. Vis. Schi., vol. 24, pp. 906–926, Jul. 1983.

Aramant; "Xenografting Human Fetal Retina to Adult Rat Retina", Suppl. Invest. Ophthalmol. Vis. Sci., 31:594, abs. #2907–5, 1990.

Aramant; "The Fate of Retinal Ganglion Cells, Retrogradely Labeled with Fluorogold and Transplanted to Rate Retina", Suppl. Invest. Ophthalmol. Vis. Sci., 32:983, abs #1545, 1991.

Aramant; "Tracing of connections Between Retinal Transplants and Host Retina with . . . ", Invest. Opththalmol. Vis. Sci., 34:1096, #4, #1935–91, Mar. 15, 1993.

Arvo; "Arvo Abstract Packet for Annual Meeting", Sarasota, Florida (May 2–May 7, 1993) Deadline for Abstract Receipt; Dec. 4, 1992.

Arvo; "Arvo Conference Brochure for Annual Meeting", Sarasota, Florida (May 2–May 7, 1993).

(List continued on next page.)

Primary Examiner—Michael Powell Buiz
Assistant Examiner—A. T. Nguyen
Attorney, Agent, or Firm—Daniel B. Schein, Esq.

[57] ABSTRACT

A method for transplanting planar implants, devices, etc., is provided. Method is particularly adapted for transplanting planar sheets of retinal cells to the subretinal region of an eye. A method of preparing the retinal cell sheet and the associated surgical instrument is also provided.

9 Claims, 15 Drawing Sheets

U.S. PATENT DOCUMENTS

| | | |
|---|---|---|
| 4,418,691 | 12/1983 | Yannas et al. . |
| 4,428,748 | 1/1984 | Peyman et al. . |
| 4,495,288 | 1/1985 | Jarvis, Jr. et al. . |
| 4,499,899 | 2/1985 | Lyons . |
| 4,563,779 | 1/1986 | Kelman . |
| 4,655,774 | 4/1987 | Choyce . |
| 4,662,869 | 5/1987 | Wright . |
| 4,689,399 | 8/1987 | Chu ............................................ 530/356 |
| 4,693,686 | 9/1987 | Sendax . |
| 4,702,697 | 10/1987 | Linkow . |
| 4,727,018 | 2/1988 | Eichner et al. ............................. 435/1 |
| 4,747,836 | 5/1988 | Luther ...................................... 604/198 |
| 4,837,857 | 6/1989 | Scheller et al. .......................... 455/617 |
| 4,861,339 | 8/1989 | Jonischkeit ............................... 604/118 |
| 4,868,116 | 9/1989 | Morgan et al. . |
| 4,871,094 | 10/1989 | Gall et al. . |
| 4,900,300 | 2/1990 | Lee . |
| 4,911,161 | 3/1990 | Schechter ................................ 606/171 |
| 4,927,676 | 5/1990 | Williams . |
| 4,940,468 | 7/1990 | Petillo . |
| 4,963,489 | 10/1990 | Naughton et al. . |
| 4,994,028 | 2/1991 | Leonard et al. ............................ 604/60 |
| 5,000,963 | 3/1991 | Hefton . |
| 5,019,035 | 5/1991 | Missirlian ................................. 604/22 |
| 5,184,625 | 2/1993 | Cottone et al. .......................... 606/205 |
| 5,275,607 | 1/1994 | Lo et al. ................................... 606/169 |
| 5,292,802 | 3/1994 | Rhee et al. . |
| 5,295,967 | 3/1994 | Rondelet et al. ......................... 604/154 |
| 5,308,343 | 5/1994 | Gafner . |
| 5,308,889 | 5/1994 | Rhee et al. . |
| 5,322,504 | 6/1994 | Doherty et al. .......................... 606/167 |
| 5,322,691 | 6/1994 | Darougar et al. . |
| 5,323,788 | 6/1994 | Silvestrini et al. . |
| 5,324,260 | 6/1994 | O'Neill et al. . |
| 5,326,346 | 7/1994 | Cortes . |
| 5,326,584 | 7/1994 | Kamel . |
| 5,328,481 | 7/1994 | Wang . |
| 5,342,370 | 8/1994 | Simon et al. . |
| 5,346,464 | 9/1994 | Camras ....................................... 604/9 |
| 5,370,658 | 12/1994 | Scheller et al. .......................... 606/205 |
| 5,374,515 | 12/1994 | Parenteau et al. ........................... 435/1 |
| 5,409,478 | 4/1995 | Gerry et al. . |
| 5,507,807 | 4/1996 | Shippert ..................................... 628/8 |

OTHER PUBLICATIONS

Axen; "Chemical Coupling of Peptides and Proteins to Polysaccharides by Means of Cyanogen Halides", nature, 214:1302–1304, Jun. 24, 1967.

"Biodegradable Polymers", Polysciences, Inc., Data Sheet #365, Jan. 1990.

Bhatt; "Transplantation of Human Retinal Pigment Epithelial Cells Into Rabbits", Invest. Ophthalmol. Vis., vol. 4, #4, abs. #1920–76, Mar. 15, 1993.

Bignami; "The Radial Glial of Muller in the Rat Retina and Their Response to Injury. An Immunofluorescence Study with Antibodies to the Glial Fibrillary Acidic (GFA) Protein", Exp. Eye Res., 28:63–69, (1979).

Bjorklund; "Neural Grafting in the Mammalian CNS", Elsevier Science Publishing B.V., Netherlands, Ch. 38, pp. 431–436, 1985.

Bonds; "Visually evoked potentials and deoxyglucose studies of monocularly deprived cats", Suppl., Invest. Ophthalmol. Visual Sci. 18:225, abs. #11, Apr. 1980.

Cameron; "The Cone Photoreceptor Mosaic of the Green Sunfish", Soc. Neuroscience, 18:838, abs. #352.6, Oct. 25–30, 1992.

Cuatrecasas; "Selective Enzyme Purification by Affinity Chromatography", Biochemistry Cuatrecases et al., 61:636–643, Aug. 9, 1968.

Custis; "Clinical Angiographic and Histopathologic Correlations in Surgically removed Subfoveal Choroidal Neovascularization", Invest. Ophthalmol. Vis. Sci., 34:834, #4, abs. #651, Mar. 15, 1993.

del Cerro; "Intraocular Retinal Transplants", Invest. Ophthalmol, Vis. Sci., vol. 26, pp. 1182–1185, Aug. 1985.

del Cerro; "Intraretinal transplantation of fluorescently labeled retinal cell suspensions", Neurosci. Lt., 92 pp. 21–26, (1988).

del Cerro, "Retinal Transplants", Progress in Retinal Research vol. 9, chapter 6, pp. 229–269, 1990.

del Cerro, "Selective Transplantation of Enriched Cell Populations Derived from Immature Rat Retina", Supp. Invest. Ophthalmol. Visual Sci., 30:208, abs. #6, 1989.

Del Priore, "Transplantation of Retinal Pigment Epithelium (RPE) Onto Bruch's Memebrane in Organ Culture", Supp., Invest. Ophthalmol. Vis. Sci. 33:1127, #4, abs. #2174, Mar. 15, 1992.

Del Priore, "Experimental and surgical aspects of retinal pigment epithelial cell transplantation", Eur. J. Implant Ref. Surg. 5:128–131, Jun. 1993.

Del Priore, "Differential ability of aged versus young human Bruch's Membrane to support repopulation by health RPE", Invest. Ophthalmol. Vis. Sci. 34:834, #4, abs. #652, Mar. 15, 1993.

Du, "Long Term Survival of Infant Versus Adult Photoreceptor Transplants Labeled by Tritiated Thymidine", Suppl. Invest. Ophthalmol. Vis. Sci. 32:983, abs. #1546, 1991.

Du, "Neonatal Mouse Photoreceptor Transplants Replace the Photoreceptor Layer of the Host", Invest Ophthalmol. Vis. Sci. 34:1096, #4, abs. #1934–90, Mar. 15, 1992.

Edwards, "Light–Regulated Protein Phosphatase Activity in Limulus Ventral Photoreceptors", Soc. Neurosci. 16:405, abs. #171.6, 1990.

Faktorovich, "Photoreceptor Degeneration in Inherited Retinal Dystrophy Delayed by Basic Fibrolast Growth Factor", Nature, 347:83–86, Sep. 6, 1990.

Faktorovich, "Basic Fibroblast Growth Factor and Local Injury Protect Photoreceptors from Light Damage in the Rat", vol. 12(9) Journal of Neuroscience pp. 3554–3567, Sep. 1992.

Fang, "Development of a surgical procedure and instrument for transplantation of extended gelatin sheets to the subretinal space", Invest. Ophthalmol. Vis. Sci. 34:1096, #4, #1918–1974, Mar. 15, 1993.

Ferguson, "Effect of genetic disparity on photoreceptor transplant survival", Invest Ophthalmol. Vis. Sci. 32:983, #4, abs. #1549, Mar. 15, 1991.

Fischer, "Photoreceptor Topography in the Retinae of Anubis Baboons", Soc. Neuroscience 18:838, abs. #352.7, Oct. 25–30, 1992.

Garcia, "Comparison of Allogeneic and Syngeneic RPE Transplants in Renal Subcapsular Space", Invest Ophthalmol. Vis. 34:1112, abs. #2017–2049, 1993.

Gao, "Low immunogenicity of neonatal murine photoreceptor cells for cytotoxict lymphocytes in mice", Invest. Ophthalmol. Vis. Sci. 33:1285, #4, #2963, Mar. 15, 1992.

Gelanze, "Survival of Photoreceptors Transplanted to the Subretinal Space of Adult RCS Rats", Suppl. Invest. Ophthalmol. Visual Sci., 30:208, abs. #8, (1989).

Gouras, "Reconstruction of Degenerate rd Mouse Retina by Transplantation of Transgenic Photoreceptors", Invest. Ophthal. & Vis. Sci., vol. 33/9, pp. 2579–2586, Aug. 1992.

Gouras, "Transplanted Photoreceptors Form Mature Outer Segments in Degenerate rd Mouse Retina", Invest. Ophthalmol. Vis. Sci. 33:1128, #4, abs #2180, Mar. 15, 1992.

Gouras, "Anatomy and Physiology of Photoreceptor Transplants in Degenerate C3H Mouse Retina", Invest. Ophthalmol. Vis. Sci. 34:1096, #4, abs. #1938–94, Mar. 15, 1993.

Hicks, "Different Rhodopsin Monoclonal Antibodies Reveal Different Binding patterns on Developing and Adult Rat Retina", Jour. of Histochemistry & Cytochemistry, vol. 35, No. 11, pp. 1317–1328, (1987).

Honig, "Fluorescent Carbocyanine Dyes Alloy Living Neurons of Identified Origin to be Studied in Long–term Cultures", Jour. of Cell Biology, 103:171–187, Jul. 1986.

Hughes, "Whole Cell Recordings of Isolated Retinal Pigment Epithelial Cells of the Frog", Soc. Neurosci. Abstr. 17:1301, abs. #360.18, 1987.

Hughes, "Transplantation of Retinal Photoreceptors to Dystrophic Retina", Society Sci. Abstr. 1277, abs. #511–16, Nov. 1988.

Hughes, "Transplanted Photoreceptors Form Synapses in Light–Damaged Retina", Suppl. Invest. Ophthalmol. Vis. Sci., 31:594, abs. #2908–6, 1990.

Hughes, "Differential survival of sensory elements in intracranial otic transplants", Soc. Neurosci., 17:1138, abs. #451.12, Nov. 10–15, 1991.

Hughes, "Quantification of synapses in light–damaged retina reconstructed by transplantation of photoreceptors", Invest. Ophthalmol. Vis. Sci., #4, 33:1058, abs. 1832–3, Mar. 15, 1992.

Hughes, "Explorations of optic transplantation", Experimental Neurology, 115:37–43, 1992.

Jacobs, "An Ultraviolet–Sensitive Cone in the Gerbil Retina", Soc. Neuroscience, 18:838, abs. #352.10, Oct. 25–30, 1992.

Jiang, "Intraocular Retinal Transplantation in Retinal Degeneration (rd/rd) Murine Strains", Suppl., Invest. Ophthalmol. Visual Sci., 30:208, abs. #5, (1989).

Kaplan, "Retinal pigment epithelium regeneration in the non–human primate", Suppl., Invest. Ophthalmol. Vis. Sci. #4, abs. #2173, Mar. 15, 1992.

Kitchell, "Poly(lactic/glycolic acid) biodegradable Drug–Polymer Matrix Systems", Methods in Enzymology, 112:436–448, Chap. 32, (1985).

Klassen, "Retinal transplants can drive a pupillary reflex in host rat brains", Proc. Natl. Acad. Sci. U.S.A., vol. 84, pp. 6958–6960, Oct. 1987.

Klassen, "Anatomical and Behavioral Correlates of a Xenograft–Mediated Pupillary Reflex", Experimental Neurology 102, 102–108, (1988).

Kordower, "Fetal Monkey Retina Transplanted into Adult Rat Eyes", Supp. Invest. Ophthalmol. Visual Sci., 30:208, abs. #7, (1989).

Kruszewska, "Ultrastructure and Transduction in the Caudal Photorecetor of Crayfish", Soc. Neurosci. 16:405, abs. #171.5, 1990.

Lane, Transplantation of Retinal Pigment Epithelium Using a Pars Plana Approach, Eye, 3:27–32, 1989.

LaVail, "Histotypic Organization of the Rat Retina in Vitro", Z. Zellforsch, Springer Verlag, 114:557–579, 1971.

LaVail, "Multiple Growth factors, Cytokines, and Neurotrophins Rescue Photoreceptors from the Damaging Effects of Constant Light", Neurobiology, vol. 89, 11249–11253, Dec. 1992.

LaVail, "RPE Cell Transplantation in RCS Rats: Normal Metabolism in Rescued Photoreceptors", Suppl., Invest. Ophthalmol. Vis. Sci. 33:1127, #4, #2176, Mar. 15, 1992.

Lee, "Transplantation of Cultured Retinal Pigment Epithelium to Rabbit Retina Injured by Sodium Iodate", Suppl., Invest. Ophthalmol. Vis. Sci. 33:1127, abs #2175, Mar. 15, 1992.

Li, "Transplantation of Retinal Pigment Epithelial Cells to Immature and Adult Rat Hosts; Short– and Long–term Survival Characteristics", Exp. Eye Res. 47:771–785 (1988).

Li, "Inherited Retinal dystropy in the RCS Rat: Prevention of Photoreceptor Degeneration by Pigment Epithelial Cell Transplantation", Exp. Eye Res. 47:911–917, (1988).

Li, "Optimal Coditions for Long–term Photoreceptor Cell Rescue in RCS Rats: The Necessity for Healthy RPE Transplants", Exp. Eye Res. 52:669–679, (1991).

Liu, "Photoreceptor inner and outer segments in transplanted retina", Soc. Neurosci., 16:405, abs. #171.1, 1990.

Liu, "Transplantation of confluent sheets of adult human RPE", Invest. Ophthalmol. Vis. Sci. 33:1128, #4, abs. #2180, Mar. 15, 1992.

Liu, "Transplantation of confluent sheets of adult human and rat RPE on a thin substrate", Suppl., Invest. Ophthalmol. Vis. 34:1112, abs. #2018–50, 1993.

Lopez, "Transplanted retinal Pigment Epithelium Modifies the Retinal Degeneration in the RCS Rat", Invest. Ophthalmol. & Vis. Sci., 30:586–589, #3, Mar. 1989.

Lopez, "Transplantation of Human RPE Cells into the Monkey", Suppl. Invest. Ophthalmol. Vis. Sci., 31:594, abs #2910–8, 1990.

Lund, "Axonal Outgrowth from Transplanted Retinae is Stimulated by Appropriated Target Regions", Suppl., Invest. Opthalmol. Visc., 28:288, abs. #12 (1987).

MacLeish, "Growth and Synapse Formation Among Major Classes of Adult Salamander Retinal Neurons in Vitro", Neuron, Vo. 1, pp. 751–760, Oct. 1988.

Mayerson, "An Improved Method for Isolation and Culture of Rat Retinal Pigment Epithelial Cells", Invest. Ophthalmol. & Vis. Sci., 26:1599–1609, Nov. 1985.

McConnell, "Regeneration of ganglion cell axons in the adult mouse retina", Brain Research, 241:362–365 (1982).

Maurice, "Keratoplasty with Cultured Endothelium on Thin Membranes", Arvo Abstracts, Supp. Inv. Ophthalmol. and Vis. Sci., p. 10, abs #9, Apr. 1979.

McCulley, "Corneal Endothelial Transplantation", Ophthalmol., vol. 87, #3, pp. 194–201, Mar. 1980.

McCulley, "A Gelatin Membrane Substrate for the Transplantation of Tissue Cultured Cells, Transplantation", vol. 29, No. 6, pp. 498–499, Jun. 1980.

Mollenhauer, "Plastic Embedding Mixtures for use in Electron Microscopy", Stain Tech., 39:111–114.

Moritera, Transplants of monolayer retinal pigment epithelium grown on biodegradable membrane in rabbits. Invest. Ophthalmol. Vis. 34: #4, abs. 1919–75, Mar. 15, 1993.

Muller, "Morphology and synaptic inputs to lucifer yellow injected bipolar cells in rat retinal slices", Soc. Neurosci., 17:1013, abs. #403.4, Nov. 10–15, 1991.

Muller, "Rod and cone inputs to bipolar cells in the rat retina", Inves. Ophthalmol. Vis. Sci. 34:984, #4, abs. #1387, Mar. 15, 1993.

Mueller, "Autotransplantation of Retinal Pigment Epithelium in Intravitreal Diffusion Chamber", vol. 80, No. 3, Part II Retinal Pigment Epithelium, pp. 530–537, 1993.

Nasir, "Choriocapillaris Atrophy as a Complication of Surgical Excision of Choroidal Neovascular Membranes", Invest. Ophthalmol. Vis. Sci. 34:834, #4, abs. #653, Mar. 15, 1993.

Newsome, "Transplantation of Human Retinal Pigment Epithelium Into Primate Model of Macular Degeneration", Retina Society Meeting, Toronto, Canada, Sep. 1991.

O'Steen, Retinal and Optic Nerve Serotonin and Retinal Degeneration as Influenced by Photoperiod, Exp. Neurology, 27:194–205, 1970.

Petry, "Immunocytochemical Identification of Photoreceptor Populations in the Retinas of Normal and Red–Light–Reared Tree Shrews", Soc. Neuroscience, 18:838, abs. #352.9, Oct. 25–30, 1992.

Pfeffer, Improved Methodology for Cell Culture of Human and Monkey Retinal Pigment Epithelium, Chapter 10, Progress in retinal research, vol. 10, pp. 251–291, 1991.

Politi, Generation of Enriched Populations of Cultured Photoreceptor Cells, Invest. Ophthalmol. Vis. Sci., vol. 27, No. 5, pp. 656–665, May, 1986.

Powell, "Controlled release of nerve growth factor from a polymeric implant", Brain Res., 515:309–311, 1990.

Pul, "Biochemical Interruption of Membrane Phospholipid Renewal in retinal Photoreceptor Cells", Jour. of Neurosci., vol. 4, No. 6, pp. 1559–1576, Jun. 1984.

Radel, "Quantification of Light–Activated Pupilloconstriction in Rats Mediated by Intracranially Transplanted Retinae", Suppl. Invest. Ophthalmol. Vis. Sci. 32:983, abs #1550, 1991.

Radtke, "Pharmacological Therapy for Proliferative Vitreoretinopathy", vol. 224 Graefe's Archive Ophthamol. pp. 230–233, 1986.

Raymond, "Progenitor Cells in Outer Nuclear Layer of Goldfish Retina That Normally Produce Only Rods Produce other Neurons during Retinal Degeneration", Suppl., Invest. Ophthalmol. Vis. Sci. 28:288, abs. #13, 1987.

Royo, "Retinal Transplantation from Fetal to Maternal Mammalian Eye", Growth, 23:313–336, 1959.

Sarthy, Isolated Cells from a Mammalian Retina, Brain Research, 176:208–212, 1979.

Schuschereba, "Retinal cell and photoreceptor transplantation between adult New Zealand Red Rabbit Retinas", Experimental Neurology. 115:95–99, 1992.

Seaton, "Inhibition of Neovascularization by the Transplantation of Healthy Retinal Pigment Epithelial Cells into the RCS Rat", Suppl., Invest. Ophthalmol. Vis. Sci. 32:983, abs. #1547, 1991.

Sheedlo, "Photoreceptor Cell Rescue by RPE–Cell Grafts in RCS Rats at Early and Late Stages of Retinal Dystrophy", Suppl., Invest. Ophthalmol. Visual Sci., 30:208, abs #10, 1989.

Sheedlo, Functional and Structural Characteristics of Photoreceptor Cells Rescued in RPE–cell Grafted Retinas of RCS Dystrophic Rats, 48:841–854, 1989.

Shiosaka, "A simple method for the separation of retinal sublayers from the entire retina with special reference to application for cell culture", Jour. Neurosci. Methods, 10:229–235, 1984.

Silverman, "Deoxyglucose mapping of Orientation and spatial frequency in cat visual cortex", Suppl., Invest. Ophthalmol. Visual Sci. 18:225, abs #10, 1980.

Silverman, "Deoxyglucose mapping of orientation in cat visual cortex", Recent Advances in Vision. Optical Society of America Technical Digest. SA13, 1980.

Silverman, "The retinotopic organization of cat striate cortex", Suppl. Invest Ophthalmol. Visual Sci. 22:105, abs. #1, 1982.

Silverman, "Department of Health and Human Services Grant Application, Transplantation of Mammalian Photoreceptors", Martin S. Silverman, pp. 1–13, submitted May, 1986, funded by NEI Sep. 11, 1986, Grant No. 1RO3 EY 06943–01.

Silverman, "Department of Health and Human Services Grant Application, Transplantation of Mammalian Photoreceptors", Martin S. Silverman, pp. 1–61, submitted May, 1987, funded by NEI Feb. 16, 1988, Grant No. 1RO1, EY07547–01.

Silverman, Transplantation of retinal photoreceptors to light damaged retina, Suppl., Invest. Ophthalmol. Vis. Sci. 28:288, abs # 11, 1987.

Silverman, Transplantation of retinal photoreceptors to light damaged retina: Survival and integration of receptors from a range of postnatal ages, Soc. Neurosci. Abstr. 17:1301, abs. #360.17, 1987.

Silverman, Transplantation of Human Photoreceptors to Light Damaged Retina, Soc. Neurosci. Abstr. 18:1278, abs. #511.17, 1988.

Silverman, "Photoreceptor transplantation in inherited and environmentally induced retinal degeneration: Anatomy, Immunohistochemistry and Function. Inherited and Environmentally Induced Retinal Degenration", (ed., MM LaVail, RE Anderson, and JG Hollyfield) Alan r. Liss publisher, pp. 687–704, 1989.

Silverman, "Photoreceptor rescue in the RCS rat without pigment epithelium transplantation", Soc. Neurosci., 15:115, abs #51.1, Oct. 29–Nov. 3, 1989.

Silverman, "Transplantation of Photoreceptors to Light Damaged Retina", Invest. Ophthalmol. Vis. Sci., vol. 30, No. 8, 1684–1690, Aug. 1989.

Silverman, Light Dependent Activation of Light Damaged Retina by Transplanted Photoreceptors, Suppl., Invest. Ophthalmol. Visual Sci., 30:208, abs. #9, 1989.

Silverman, "Transplantation of Human and Non–Human Primate Photoreceptors to Damaged Primate Retina", Invest. Ophthalmol. Visual Sci., 31:594, abs #2909–7, 1990.

Silverman, "Photoreceptor rescue in the RCS rat without pigment epitheliium transplantation", Curr. Eye Res. 9:183–192, #2, 1990.

Silverman, "Photoreceptor transplantation to dystrophic retina. Retinal Degeneration", (ed. Anderson R.E., LaVail, MM, and Hollyfield J.G.). CRC Press, Inc., Boca Raton, Florida, pp. 321–335, Chapter 29, 1991.

Silverman, Silverman Confidential letter from Central Institute for the Death at Washington University Medical Center, dated Oct. 7, 1991 to Gholam A. Peyman, M.D. and attachments.

Silverman, "Restoration of the pupillary reflex by photoreceptor transplantation", Supp. Invest. Ophthalmol. Vis. Sci. 32:983, abs #1548, 1991.

Silverman, Effect of Genetic Disparity on Photoreceptor Transplant Survival, Supp., Invest. Ophthalmol. Vis. Sci. 32:983, abs #1549.

Silverman, "Photoreceptor transplantation: Anatomic, electrophysiologic and behavioral evidence for the functional reconstruction of retinas lacking photoreceptors". Soc. Neurosci. 17:12, abs. #9.4, Nov. 10–15, 1991.

Silverman, "Photoreceptor transplantation: Anatomic, electrophysiologic and behavioral evidence for the functional reconstruction of retinas lacking photorecptors", Experimental Neurology 115:87–94, 1992.

Silverman, "Rescue of host cones by transplanted donor photoreceptors in the rd mouse", Invest. Ophthamol. Vis. Sci. 34:1096, #4, abs. #1937–93, Mar. 15, 1993.

Silverman, Transplantation of Retinal Photoreceptors to Light–Damaged Retina, 288 Arvo Abstracts, abs. #11.

Silverman, "A comparison of Ocular Dominance Patterns in Cat and Monkey", Suppl. Invest. Ophthalmol. Visual Sci. 22:12, #3, abs. #13, Mar. 1982.

Simmons, "Physiological Responses in Retinal Transplants and Host Tecta Evoked by Electrical or Photic Stimulation of Transplanted Embryonic Retinae", Soc. Neurosci. Abstr. 10:668, abs #196.5.

Sokoloff, "the [C]Deoxyglucosel Method for the Measurement of Local Cerebral Glucose Utilization: Theory, Procedure, and Normal Values in the Conscious and Anesthetized Albino Rat", Jour. of Neurochem., 28:897–916, 1977.

Solomons, Special Topic M Photochemistry of Vision Organic Chemistry. 5th Ed., Univ. of FL, Pub. Wiley & Sons, pp. 1168–1171, 1991.

Tien, In Search of A Receptor for Outer Segments in Rat Retinal Pigmented Epithelium, Soc. Neurosci. 16:405, abs #171.3, 1990.

Tootell, "Deoxyglucose mapping of color and spatial frequency organization in monkey and Cat Cortex", Recent Advances in Vision. Optical Society of America Techn. Digest. SA14, 1980.

Tootell, "Color–Dependent Deoxyglucose Patterns Within Macaque Cortex". Arvo Abstracts 226, Suppl. Invest. Ophthalmol. Vis. Sci. pp. 226, abs. #12, Apr. 1980.

Tootell, "2DG study of retinotopic organization in macaque striate cortex", Suppl., Invest. Ophthalmol. Visual Sci. 22:12, #3, abs. #14, Mar. 1982.

Tootell, "Deoxyglucose analysis of retinoptic organization in primate striate cortex", Sci. 218:902–904, Nov. 26, 1982.

Tootell, "Two methods for flat–mounting cortical tissue", Journal Neurosci. Methods, 15:177–190, 1985.

Townes, "Rod Photoreceptors Dissociated from the Adult Rabbit Retina", Jour. of Neuroscience, vol. 8, No. 1, pp. 320–331, Jan., 1988.

Tuliusson, Reversed Ratio of Color Specific Cones in Rabbit Retinal Transplants, Invest. Ophthalmol. Vis. Sci. 34:1096, abs. #1936–92, Mar. 1993.

Turner, "Newborn Rat Retinal Cells Transplanted Into a Retinal Lesion Site In Adult Host Eyes", Develop. Brain Research, 26:91–104, (1986).

Valentino, Transplanted photoreceptors form synapses in reconstructed RCS rat retina. Soc. Neurosci., 16:405, abs #171.2, Oct. 28–Nov. 2, 1990.

Valentino, "Photoreceptor rescue in RCS rat and rd mouse by head shock", Suppl., Invest. Ophthalmol. Vis. Sci., 31:594, abs. #2911–9, 1990.

Valentino, "Photoreceptor sheets isolated from the neonatal rat retina lack synapses and other retinal cells", Soc. Neuroscience. 18:838, abs. #352–8, Oct. 25–30, 1992.

Vinores, "Ultrastructural Localization of RPE Epitopes and In Situ and Clutrued RPE Cells and their Expression in Fibroblasts in Vitreous Culture", Soc. Neurosci. 16:405, abs. #171.4, 1990.

Weiss, Transplanting the Light Fantastic Cells from eye donors may someday restore vision in some blind individuals, Science News, vol. 136, No. 19, pp. 297–300, Nov. 4, 1989.

Wilcheck, "Immobilization of Enzymes and Affinity Ligands onto Agarose Via Stable and Uncharged Carbamate Linkages", Biochem. Int'l. vol. 4, No. 6, pp. 629–635, Jun. 1982.

Wise, Lactic/Glycolic Acid Polymer, Drug Carriers in Biology and Medicine (ed. Gregoriaris) 1979 Chapter 12, pp. 237–270.

Zucker, "Synaptic Microcircuitry of Rat Retinal Transplants Ultrastructural Observations", Suppl., Invest. Ophthalmol. Vis. Sci., 31:594, abs. #2906–4, 1990.

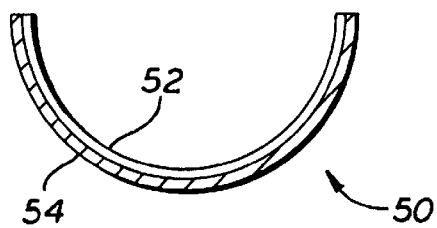
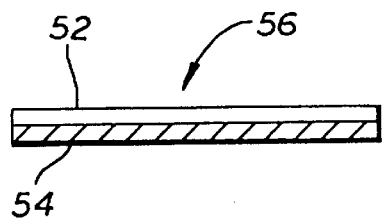
FIG. 3
FIG. 4
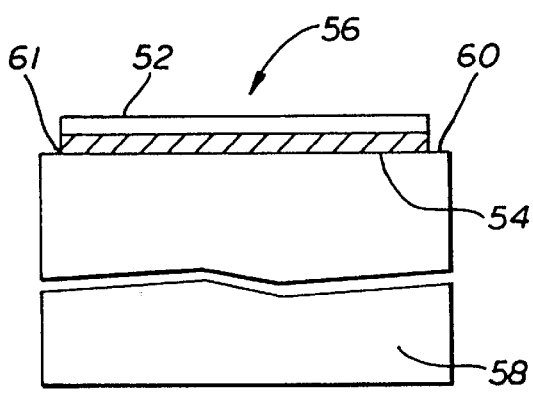
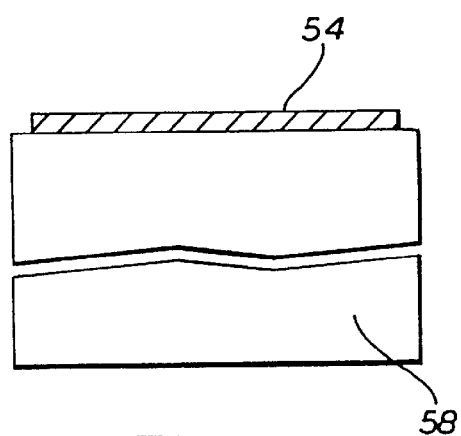
FIG. 5
FIG. 6
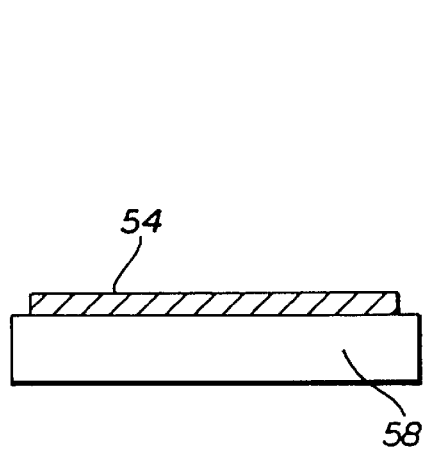
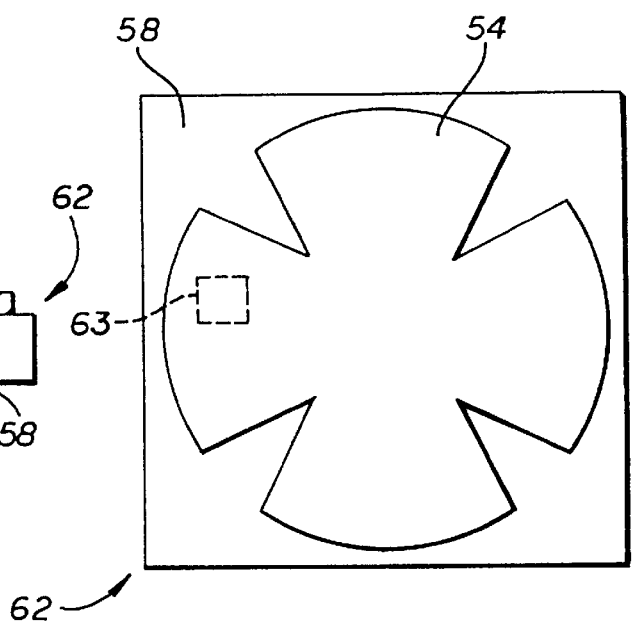
FIG. 7
FIG. 8

METHOD FOR PREPARATION AND TRANSPLANTATION OF PLANAR IMPLANTS AND SURGICAL INSTRUMENT THEREFOR

BACKGROUND OF THE INVENTION

This application is related to U.S. patent application Ser. No. 08/057,144 which is a continuation-in-part of copending application Ser. Nos. 08/033,105, filed Mar. 16, 1993 now abandoned, and 08/322,735 filed Oct. 13, 1994 which is a continuation of 07/566,996, filed Aug. 13, 1990 now abandoned which in turn is a continuation-in-part of application Ser. No. 07/394,377 filed Aug. 14, 1989, now abandoned.

The present invention relates in general to surgical instruments and surgical techniques. More particularly, the present invention in one aspect is directed to a surgical tool for transplanting planar sheets of retinal cells, epithelial tissue and/or choroidal tissue in a volute configuration through a standard sized incision in the eye, a graft for transplantation to the subretinal region of the eye, a method for preparing such grafts for transplantation and a method for reconstructing dystrophic retinas, retinal pigment epithelial layers and choroids.

The retina is the sensory epithelial surface that lines the posterior aspect of the eye, receives the image formed by the lens, transduces this image into neural impulses and conveys this information to the brain by the optic nerve. The retina comprises a number of layers, namely, the ganglion cell layer, the inner plexiform layer, inner nuclear layer, outer plexiform layer, outer nuclear layer, photoreceptor inner segments and outer segments. The outer nuclear layer comprises the cell bodies of the photoreceptor cells with the inner and outer segments being extensions of the cell bodies.

The choroid is a vascular membrane containing large branched pigment cells that lies between the retina and the sclerotic coat of the vertebrate eye. Immediately between the choroid and the retina is the retinal pigment epithelium which forms an intimate structural and functional relationship with the photoreceptor cells.

Several forms of blindness are primarily related to the loss of photoreceptor cells caused by defects in the retina, retinal pigment epithelium, choroid or possibly other factors (e.g. intense light, retinal detachment, intraocular bleeding). In several retinal degenerative diseases select populations of cells are lost. Specifically, in macular degeneration and retinitis pigmentosa, the retinal photoreceptors degenerate while other cells in the retina as well as the retina's central connections are maintained. In an effort to recover what was previously thought to be an irreparably injured retina, researchers have suggested various forms of grafts and transplantation techniques, none of which constitute an effective manner for reconstructing a dystrophic retina.

The transplantation of retinal cells to the eye can be traced to a report by Royo et al., Growth 23: 313–336 (1959) in which embryonic retina was transplanted to the anterior chamber of the maternal eye. A variety of cells were reported to survive, including photoreceptors. Subsequently del Cerro was able to repeat and extend these experiments (del Cerro et al., Invest. Ophthalmol. Vis. Sci. 26: 1182–1185, 1985). Soon afterward Turner, et al. Dev. Brain Res. 26:91–104 (1986) showed that neonatal retinal tissue could be transplanted into retinal wounds.

In related studies, Simmons et al., Soc. Neurosci. Abstr. 10: 668 (1984) demonstrated that embryonic retina could be transplanted intracranially, survive, show considerable normal development, be able to innervate central structures, and activate these structures in a light-dependent fashion. Furthermore, these intracranial transplants could elicit light-dependent behavioral responses (pupillary reflex) that were mediated through the hosts nervous system. Klassen et al., Exp. Neurol. 102: 102–108 (1988) and Klassen et al. Proc. Natl. Acad., Sci. USA 84:6958–6960 (1987).

Li and Turner, Exp. Eye Res. 47:911 (1988) have proposed the transplantation of retinal pigment epithelium (RPE) into the subretinal space as a therapeutic approach in the RCS dystrophic rat to replace defective mutant RPE cells with their healthy wild-type counterparts. According to their approach, RPE was isolated from six- to eight-day old black eyed rats and grafted into the subretinal space by using a lesion paradigm which penetrates through the sclera and choroid. A 1 ml injection of RPE (40,000–60,000 cells) was made at the incision site into the subretinal space by means of a 10 ml syringe to which was attached a 30 gauge needle. However, this method destroys the cellular polarity and native organization of the donor retinal pigment epithelium which is desirable for transplants.

del Cerro, (del Cerro et al., Invest. Ophthalmol. Vis. Sci. 26: 1182–1185, 1985) reported a method for the transplantation of tissue strips into the anterior chamber or into the host retina. The strips were prepared by excising the neural retina from the donor eye. The retina was then cut into suitable tissue strips which were then injected into the appropriate location by means of a 30 gauge needle or micropipette with the width of the strip limited to the inner diameter of the needle (250 micrometers) and the length of the strip being less than 1 millimeter. While del Cerro reports that the intraocular transplantation of retinal strips can survive, he notes that the procedure has some definite limitations. For instance, his techniques do not allow for the replacement of just the missing cells (e.g. photoreceptors) but always include a mixture of retinal cells. Thus, with such a transplant appropriate reconstruction of the dystrophic retina that lacks a specific population of cells (e.g., photoreceptors) is not possible.

del Cerro et al., Neurosci. Lett. 92: 21–26, 1988, also reported a procedure for the transplantation of dissociated neuroretinal cells. In this procedure, the donor retina is cut into small pieces, incubated in trypsin for 15 minutes, and triturated into a single cell suspension by aspirating it through a fine pulled pipette. Comparable to the Li and Turner approach discussed above, this procedure destroys the organized native structure of the transplant, including the donor outer nuclear layer; the strict organization of the photoreceptors with the outer segments directed toward the pigment epithelium and the synaptic terminals facing the outer plexiform layer are lost. Furthermore, no means of isolating and purifying any given population of retinal cells (e.g. photoreceptors) from other retinal cells was demonstrated.

It is believed that it is necessary to maintain the photoreceptors in an organized outer nuclear layer structure in order to restore a reasonable degree of vision. This conclusion is based on the well known optical characteristics of photoreceptors (outer segments act as light guides) and clinical evidence showing that folds or similar, even minor disruptions in the retinal geometry can severely degrade visual acuity.

SUMMARY OF THE INVENTION

Among the objects of the present invention, therefore, may be noted the provision of a method which conserves relatively large expanses of tissue harvested from a donor eye; the provision of such a method in which a relatively large expanse of harvested tissue is so formed as to enable the harvested tissue to be inserted into a standard-sized incision in the eye; the provision of such a method in which the polarity and organization of the cells at the time of harvest are maintained in the graft; and the provision of a method for implantation of grafts to the subretinal area of an eye.

Further among the several objects and features of the present invention may be noted the provision of a graft for use in the reconstruction of a dystrophic retina or rescue of endogenous photoreceptor cells of an individual afflicted with an inherited or acquired retinal disease which causes a progressive loss of rods and subsequent eventual cone dystrophy, dysfunction and/or loss; the provision of such a graft which facilitates regrowth of photoreceptor axons by maintaining the polar organization of the photoreceptor and the close proximity of their postsynaptic targets with the adjacent outer plexiform layer upon transplantation.

Further among the several objects and features of the present invention may be noted the provision of a surgical tool for use in the implantation method which forms planar grafts of a configuration and size capable of insertion into a standard-sized incision such as that used in conventional vitreoretinal surgery; and the provision of a surgical tool for use in the transplantation method of such grafts and other materials and devices which allows appropriate retinotopic positioning and which helps protect photoreceptors, retinal pigment epithelial tissue, choroidal tissue and/or Bruch's membrane from damage prior to and as the surgical device is positioned in the eye.

Generally, the implantation method comprises coiling an implantable material which is of sheet-like form to form a volute. In a preferred embodiment, the opposite sides of the sheet forming the volute are free of one another for subsequent uncoiling of the implantable material substantially to its original sheet-like form after expulsion from a device to be described below. An incision is made in the host eye for the insertion of the volute to a position between the retina and the underlying tissue of the host eye. The incision is smaller than the incision that would be required for insertion of the implantable material in its uncoiled sheet-like form. The volute is inserted one end first into the host eye through the incision to a position between the retina and the underlying tissue. The volute uncoils after its insertion to lie in sheet-like form between the retina and the underlying tissue of the host eye and the incision is closed.

Generally, the planar sheet for implantation comprises a layer of a non-toxic flexible composition which substantially dissolves at body temperature and a material such as a tissue graft to be implanted coiled to form a volute. The volute is inserted one end first through the incision dimensioned in accordance with the cross-sectional area of the volute to a position for implantation, and then uncoiled to lie in sheet-like form at the site of implantation. It should be noted that the surgical delivery device may also be used to deliver other forms of material such as solids, devices, or non-coiled sheets.

Generally, the components of the instrument for the formation and implantation of a volute comprises a first tubular body open at one end and having a funnel shaped interior bore. A sheet or carrier enters one end first in the tubular body at the open end thereof and is fed along the body into and through the funnel. The engagement of the carrier (e.g. a planar sheet of material carrying a drug tissue graft, etc.) as it is fed through the funnel engages with an interior surface of the funnel which causes the carrier to coil into a volute. The volute exits from a small end of the funnel where it is fed into a second tubular body. After the volute is fed into the second tubular body, the first tubular body is removed therefrom. The volute is then sealed inside of the second tubular body for packaging and transportation.

The second tubular body has a tubular tip having a beveled edge to facilitate insertion into an incision in the host eye. The second tubular body is contained in a housing which facilitates sealing as well as connection to a handpiece which allows for easier manipulation during implantation. The volute is fed through the second tubular body and into the host eye.

Other objects and features of the invention will be in part apparent and in part pointed out hereinafter.

BRIEF DESCRIPTION OF THE DRAWINGS

FIG. 3 is a schematic of a donor retina.

FIG. 4 is a schematic of a flattened retina.

FIG. 5 is a schematic of a flattened retina mounted to a substrate.

FIG. 6 is a schematic of a sectioned retina mounted to a substrate.

FIG. 7 is a schematic of a laminate comprising a retina section on a supporting, stabilizing substrate.

FIG. 8 is a schematic top plan view of the laminate of FIG. 7, showing a graft (dashed lines) comprising a photoreceptor cell layer and a supporting, stabilizing substrate.

DETAILED DESCRIPTION

As used herein, the term "donor" shall mean the same or different organism relative to the host and the term "donor tissue" shall mean tissue harvested from the same or different organism relative to the host.

Figure 1:
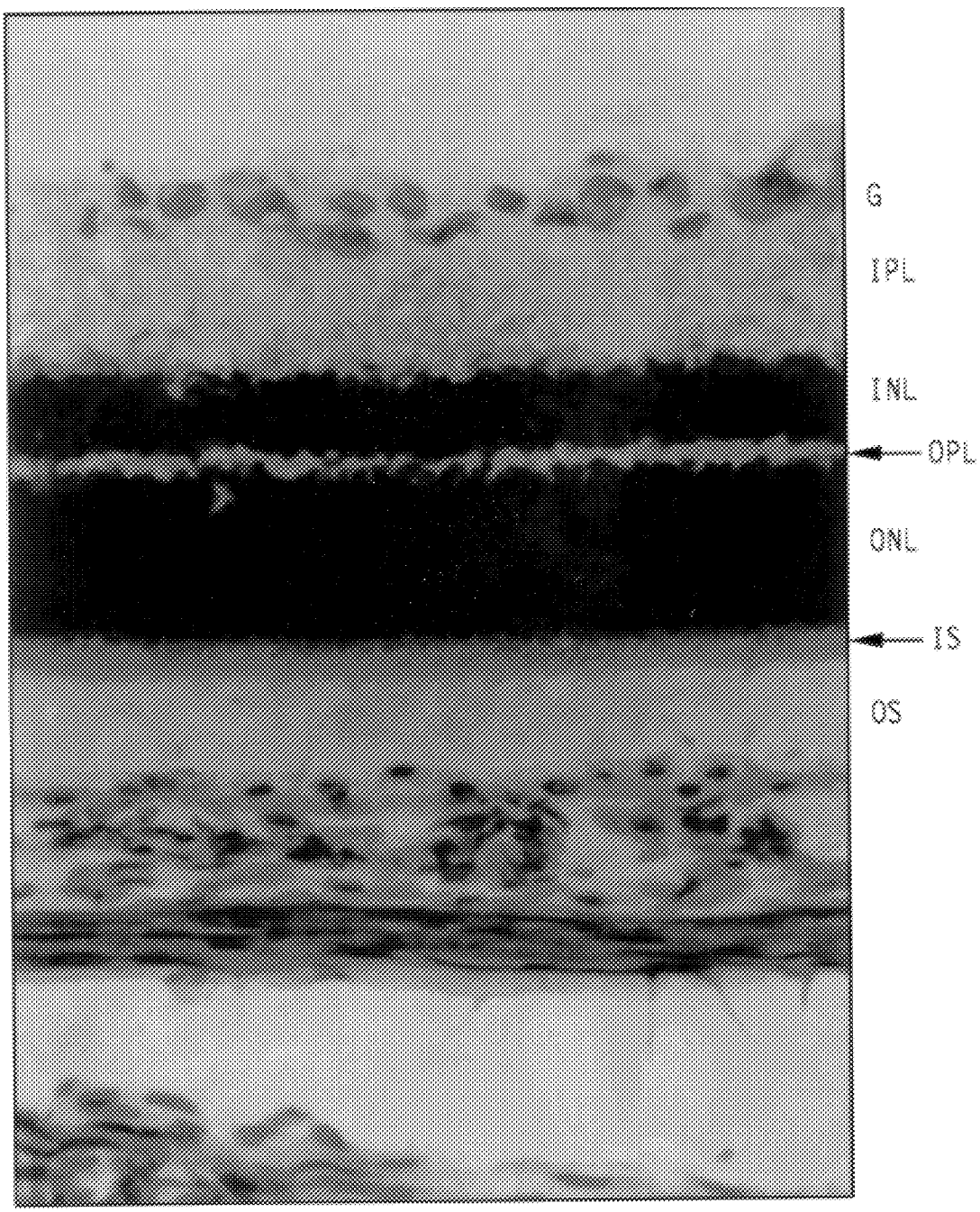
FIG. 1 is a photograph of a cryostat section of normal rat retina as set forth in example 1.
Figure 2:
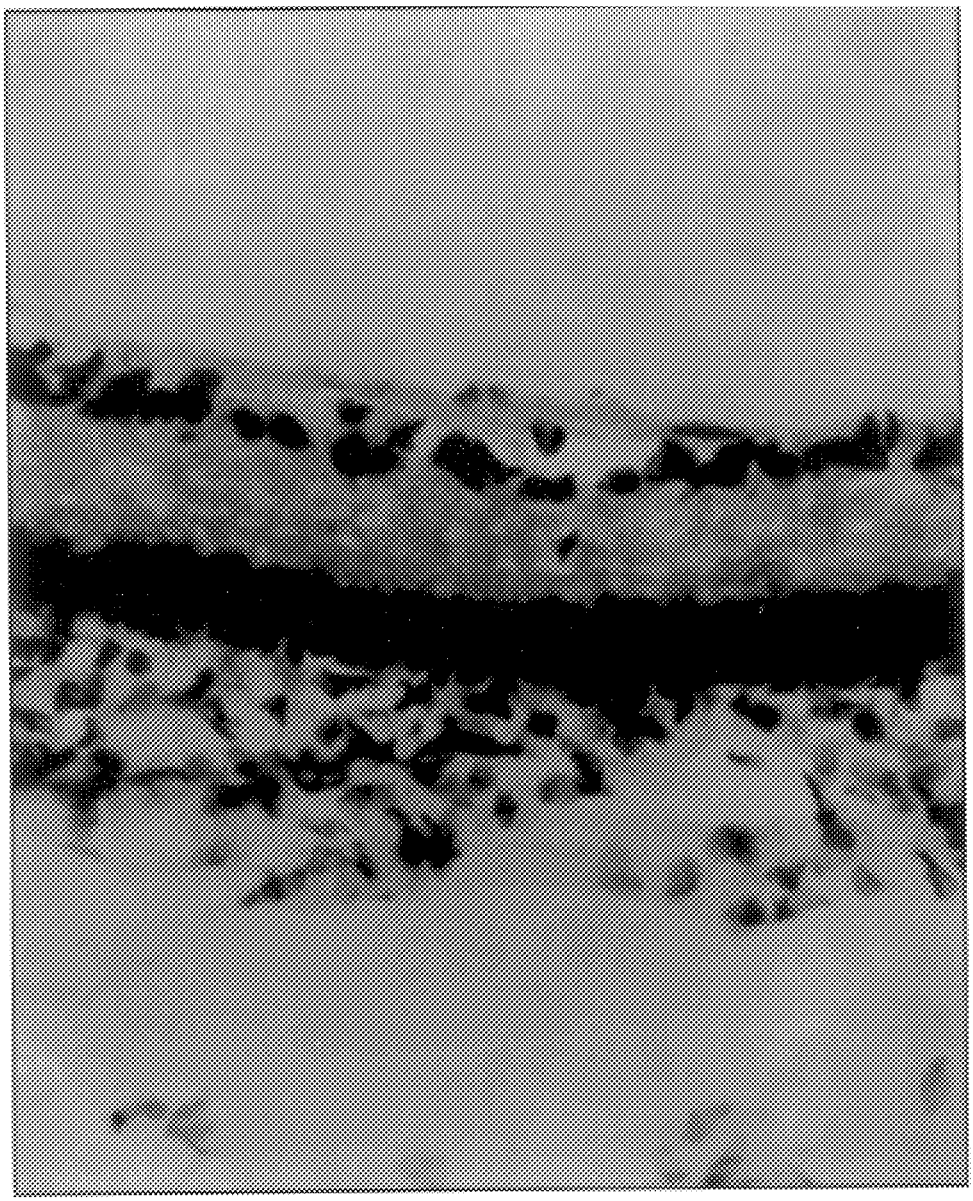
FIG. 2 is a photograph of a blinded rat retina following constant illumination as set forth in Example 1.

Several forms of blindness such as retinitis pigmentosa, retinal detachment, macular degeneration, and light exposure-related blindness, are primarily related to the loss of the photoreceptors in the eye. However, destruction of the photoreceptors does not necessarily lead to the loss of the remaining retina or axons that connect the retina to the brain. It is believed that some degree of vision can be restored, or vision loss may be slowed, by replacing damaged photoreceptors with photoreceptors harvested from a donor and which are maintained in their original organization and cellular polarity. Furthermore, as further described in co-pending Application No 08/033,105 (which is incorporated herein by reference), the transplantation of photoreceptor rods harvested from a donor eye can "rescue" endogenous cone photoreceptors within the retina and thus may restore or preserve visual sensitivity of existing cone photoreceptors. That is, it has been found that transplanted rods exert a trophic effect upon endogenous cone photoreceptors. FIG. 1 is a photograph of a cryostat section of normal rat retina. FIG. 2 is a photograph of a cryostat section Of a rat retina following constant illumination which destroys the photoreceptor (outer nuclear) layer while leaving other retinal layers and cells largely intact. In these and subsequent figures, the retina or layers thereof, e.g., the ganglion cell layer ("G"), inner plexiform layer ("IPL"), inner nuclear layer ("INL"), outer plexiform layer ("OPL"), outer nuclear layer ("ONL"), inner segments ("IS"), outer segments ("OS"), and retinal pigment epithelium ("RPE"), are shown, respectively, from top to bottom.

Referring now to FIG. 3, a photoreceptor graft for implantation through an incision smaller than the width of the graft in sheet-like form is prepared in accordance with a method of the present invention. The graft, however, may comprise other implantable material such as other retinal cells, antiviral and antibiotic agents and/or other pharmacologic agents.

A graft comprising photoreceptor cells is prepared by removing a donor retina 50 comprising inner retinal layers 52 and a photoreceptor layer 54 from a donor eye. The donor retina 50 is flattened (FIG. 4) by making a plurality of cuts through the retina from locations near the center of the retina to the outer edges thereof (see FIG. 8). Cuts can be made in other directions if necessary.

As shown in FIG. 5, the flattened retina 56 is placed with the photoreceptor side 54 down on a gelatin slab 58 which has been surfaced so as to provide a flat surface 60 that is parallel to the blade of a vibratome apparatus. The gelatin slab 58 is secured to a conventional vibratome chuck of the vibratome apparatus. Molten four to five per cent gelatin solution is deposited adjacent the flattened retina/gelatin surface interface 61 and is drawn by capillary action under the flattened retina 56 causing the flattened retina to float upon the gelatin slab 58. Excess molten gelatin is promptly removed and the floating flattened retina 56 is then cooled to approximately 4° C. with ice-cold Ringers solution that surrounds the gelatin block to cause the molten gelatin to gel. The flattened retina 56 is thereby adhered to the gelatin block 58.

As shown in FIG. 6, the inner retina portion 52 is sectioned from the top down at approximately 20 to 50 millimicrons until the photoreceptor layer 54 is reached, thereby isolating the photoreceptor layer from the inner layers of the retina, i.e., the ganglion cell layer, inner plexiform layer, inner nuclear layer, and outer plexiform layer. When the photoreceptor layer 54 is reached, the vibratome stage is advanced and a section from approximately 200 to 300 millimicrons thick is obtained as shown in FIG. 7. The thickness of this section should be sufficient to undercut the photoreceptor and form a section 62 consisting of a layer of photoreceptor cells and a thin gelatin substrate 58 adhered thereto. As shown in FIG. 8, the section 62 is cut vertically along the dashed lines to create a laminate 63.

Figure 9:
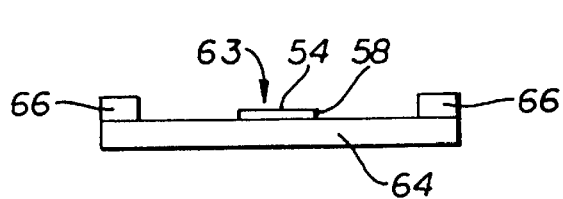
FIG. 9 is a schematic of the graft mounted on a plate formed with spacers.
Figure 10:
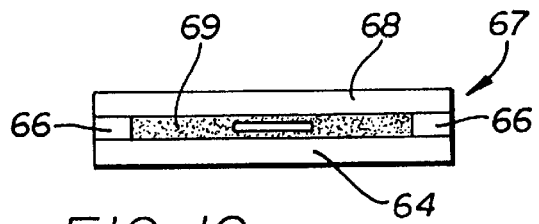
FIG. 10 is a schematic of the graft mounted on a plate infused with molten gelatin with a cover plate.

The laminate 63 is then placed onto a flat plate 64 formed with risers 66 as shown in FIG. 9. The plate 64, with the laminate 63 positioned between the risers 66, is infused with molten fifteen to twenty per cent gelatin solution to surround and cover the photoreceptor layer 54 with the gelatin substrate 58 is surrounded and covered by the molten gelatin. As shown in FIG. 10, a flat cover plate 68 is placed on top of the risers 66 to remove any excess molten gelatin and to establish the precise thickness of the graft. The height of the risers 66 can be adjusted to prepare grafts of different thicknesses.

The resulting container 67 consisting of two plates 64, 68 separated by risers 66 encasing a gelatin slab 69 with the photoreceptor layer 54 embedded therein is cooled to room temperature to cause the molten gelatin to gel and form a carrier sheet 70 encapsulating the photoreceptor layer 54. The outer segment (not shown) of the photoreceptor layer 54 faces toward one face 71 of the carrier sheet 70.

Figure 11:
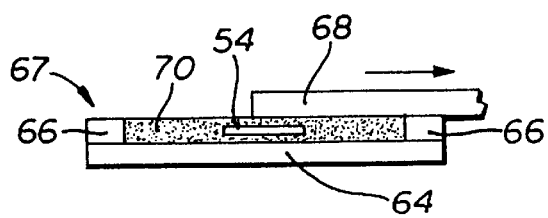
FIG. 11 is a schematic of the top plate being laterally slid off.
Figure 12:
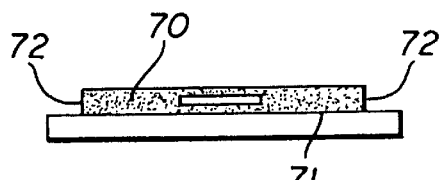
FIG. 12 is a schematic of the resulting graft.

As shown in FIG. 11, after the molten gelatin is allowed to gel, the top cover plate 68 of the laminate is carefully removed by sliding the plate laterally away from the risers 66 so as to prevent any tearing of the gelatin carrier sheet 70 and layer of photoreceptors 54. The risers 66 are likewise removed to expose the carrier sheet 70. To further reduce the risk of tearing the gelatin carrier sheet 70 upon removal of the top cover plate 68 the top cover plate can be wrapped in a TEFLON film (not shown) so that the bottom surface of the cover plate has a smooth layer of film affixed thereto. The top cover plate is removed by unwrapping the film on the upper surface of the cover plate and lifting the plate from the risers 66. The TEFLON film is then carefully peeled from the gelatin carrier sheet 70.

Figure 13:
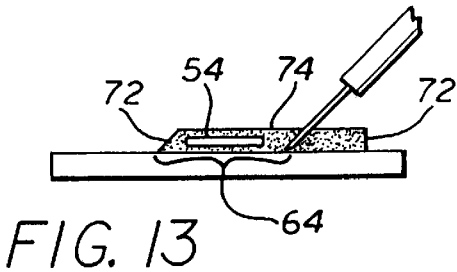
FIG. 13 is a schematic of the graft being skived.

Opposite ends 73 of the carrier sheet 70 are cut vertically to a size appropriate for transplantation. As shown in FIG. 13, opposite sides 72 of the carrier sheet 70 can be skived— cut at obtuse and acute angles relative to the top and bottom surfaces of the gelatin slab—to produce a graft 74 having approximately parallel sides. The skived sides 72 of the graft 74 facilitates the sliding of one side 72 of the graft over the other side. The surface of the graft 74 should have a surface area greater than about 1 square millimeter, preferably greater than 4 square millimeters or as large as may be practically handled within a surgical instrument for implantation of the graft through an incision in a host eye. Thus constructed, the graft 74 may subtend a considerable extent of the retinal surface.

Figure 15:
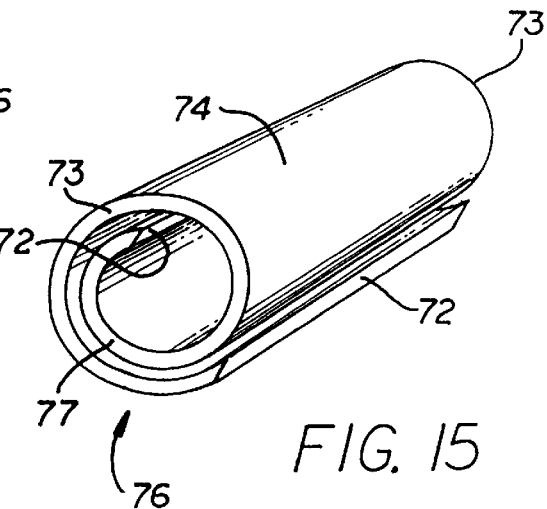
FIG. 15 is a perspective view of a volute.
Figure 14:
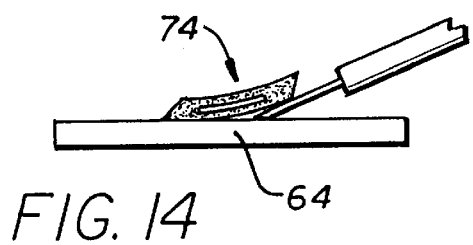
FIG. 14 is a schematic of the skived graft being removed from the plate for transplantation.

To prepare the graft for insertion into the eye, the graft 74 is removed from the plate 64 (FIG. 14) and formed into volute 76 (FIG. 15) having overlapping sides 72 and convolutions 77. The convolutions 77 of the volute 76 are free of one another in the sense that the convolutions do not impede the volute from subsequent uncoiling. Although it is not presently preferred, the sides 72 of the volute 76 do not necessarily need to overlap; any coiled configuration of the graft 74 whereby the diameter of the volute is less than the distance between the sides 72 of the uncoiled, sheet-like graft and whereby the photoreceptor layer 54 is not damaged may be prepared in accordance with the present invention.

The thickness of the graft 74 comprising the sectioned flattened retinal tissue 54 and the carrier sheet 70 as discussed above is only approximate and will vary as donor material varies. In addition, sectioning may be facilitated and vibratome thickness further calibrated from histological measurements of the thickness of the retina, thereby providing further guides to sectioning depth. Appropriate sectioning thicknesses or depth may be further determined by microscopic examination and observation of the sections.

The gelatin carrier sheet 70 adds mechanical strength and stability to the easily damaged photoreceptor layer 54. As a result, the flattened retinal tissue 54 is less likely to be damaged and is more easily manipulated during the transplantation procedure. Gelatin is presently preferred as an encapsulant because of its flexibility, pliability, ability to dissolve at body temperature and apparent lack of toxicity to neural tissue upon dissolution. However, other compositions such as ager or agarose which also have the desirable characteristics of gelatin may be substituted. Significantly, gelatin has not been found to interfere with tissue growth or post-transplant interaction between the graft 74 and the underlying retinal pigment epithelium. Gelatin is also presently preferred as an adhesive to laminate the retinal tissue 54 within the encapsulant. However, other compositions, including lectins such as concanavalin A, wheat germ agglutin, or photo reactive reagents which gel or decompose upon exposure to light and which also have the desirable characteristics of gelatin may be substituted as the adhesive.

Advantageously, the gelatin carrier sheet 70 or other encapsulant may additionally serve as a carrier for any of a number of trophic factors such as fibroblast growth factor, pharmacologic agents including immunosuppressants such as cyclosporin A, anti-inflammation agents such as dexamethasone, anti-angiogenic factors, anti-glial agents, and anti-mitotic factors. Upon dissolution of the encapsulant, the factor or agent becomes available to impart the desired effect upon the surrounding tissue. The dosage can be determined by established experimental techniques. The encapsulant may contain biodegradable polymers to act as slow release agents for pharmacologic substances that may be included in the encapsulant.

As an alternative to mechanical, e.g., microtome sectioning, the donor retina 50 may be chemically sectioned. Specifically, it is known that neurotoxic agents such as kainic acid or anoxia are toxic to cells in all retinal layers 52 except to photoreceptors and Muller cells. Therefore if the donor retina 50 is treated with an appropriate neurotoxic agent the photoreceptor layer 54 can be isolated. This technique has the advantage of maintaining the retinal Muller cells (which are relatively insensitive to kainic acid and anoxia) with the photoreceptor cells 54. Since it is known that Muller cells help maintain photoreceptor cells 54 (both biochemically and structurally) the isolation of Muller cells along with the photoreceptor cells could be advantageous.

If desired, the graft 74 may contain retinal pigment epithelial cells. Because the RPE is tenuously adherent to the retina, mechanical detachment of the retina from a donor eye ordinarily will cause the RPE to separate from the retina and remain attached to the choroid. However, through the use of enzymatic techniques such as those described in Mayerson et al., Invest. Opthalmol. Vis. Sci. 25: 1599–1609, 1985, the retina can be separated from the donor eye with the RPE attached. Alternatively, implants comprising a monolayer of RPE cells can be prepared by harvesting RPE cells from donor tissue and apposing the harvested RPE cells as an intact monolayer to a non-toxic, flexible composition, or by seeding such a composition with a monolayer of dissociated RPE cells and allowing them to grow into a confluent layer. The flexible composition serves as a stabilizing support for the RPE cells during encapsulation and transplantation.

In an alternative embodiment, a vibratome may be used to isolate retinal cell layers from a flattened retina held on a flat surface, such as applying a vacuum to a porous support on which the retina rests.

Grafts comprising the choroid, Bruch's membrane or a synthetic Bruch's membrane (e.g., collagen sheet on the order of 1–5 microns) may also be prepared. The choroid is stripped off of the scleral lining of the eye (with or without the RPE attached) and flattened by making radial cuts. The donor choroid may be encapsulated as previously described for the photoreceptor cells and/or combined with a photoreceptor layer 54 which has been prepared as described above to form a laminate comprising a photoreceptor layer and a choroidal layer encapsulated within a gelatin substrate and superstrate.

Figure 16:
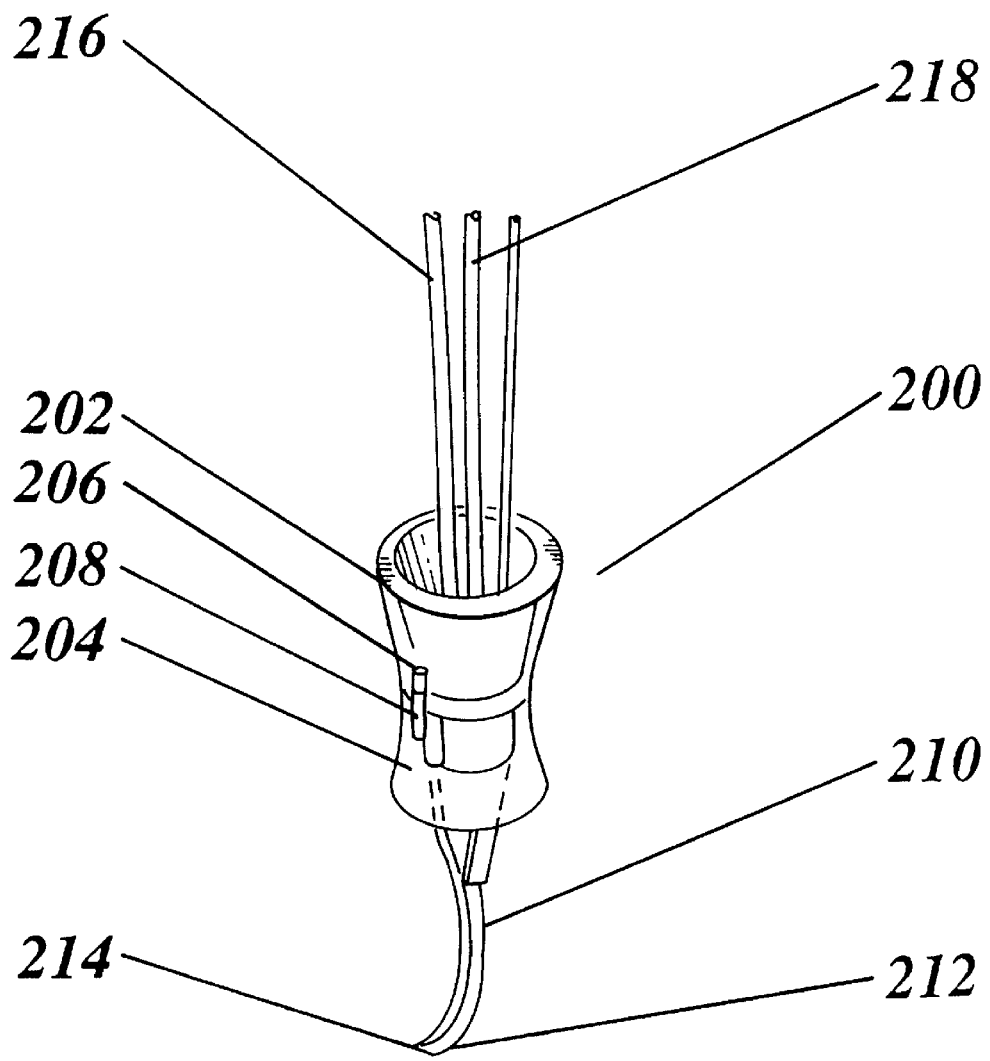
FIG. 16 is a perspective view of a surgical instrument for implantation of the graft.

Referring to FIG. 16, there is shown a handpiece 200 for an embodiment of a surgical instrument for implanting a volute 76 at a site in a host eye. The surgical instrument and method of this invention are particularly adapted for the isolation and transplantation of an intact sheet of cells from a donor retina (donor graft) to a recipient retina through an incision which is smaller than the incision that would be required for the insertion of a donor graft in its uncoiled sheet-like form and the instrument and method are further characterized by the maintenance of cell organization of the transplanted tissue layer,(e.g. the cells forming the graft have substantially the same spatial relationship with respect to one another in the graft as in the host prior to isolation).

The instrument comprises a handpiece 200, preferably made of plastic, the handpiece having a male section 202 and a female section 204 which are adapted for releasable locking engagement. The plastic may be plastic currently sold under the trademark Delrin®. Notches 206 and 208 allow for proper orientation of the male section 202 with the female section 204 as will be explained later. The female section or fitting 204 contains a delivery cannula 210, the delivery cannula 210 having a tubular tip 212 for insertion into the host eye, the tubular tip having an opening 214 for ejecting a volute or other material or device contained in cannula 210. The handpiece 200 facilitates manipulation of the delivery cannula during implantation of an implant in cannula 210.

Figure 17:
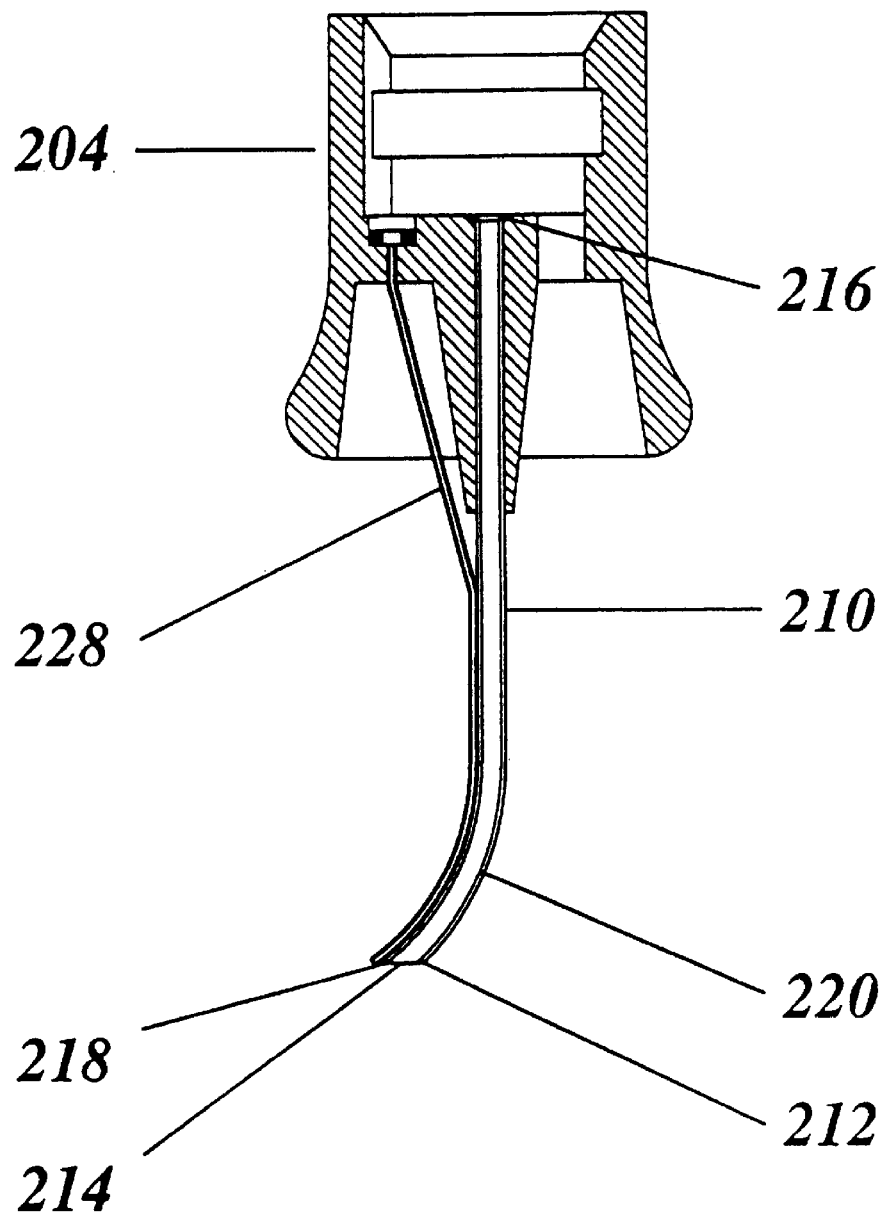
FIG. 17 is a cross sectional side view of a fitting for the surgical instrument comprising a delivery cannula mounted in a supporting housing.

Referring now to FIG. 17 a sectional view of the female fitting 204 for the delivery cannula 210 is shown. The delivery cannula 210 may be made from acrylic, glass, or some other suitable material that is sterilizable and preferably transparent to allow for viewing of material therein. The delivery cannula 210 has a tubular main body with a flared opening 216 at its distal end for smoothing the receipt of a volute as will be explained later. As shown and described herein the delivery cannula 210 preferably has an inner diameter of about 0.043 inches and is approximately 1 inch long which is an appropriate length for making implants in rodents and primates. In one embodiment the inner diameter of the tubular tip 212 must be sized to allow an intact coiled structure—i.e., a volute shaped implant—to pass therethrough for implantation without causing the opposite sides of the sheet in convolutions 77 of the volute to rub against each other and create shear stress on one another and thus possibly cause damage to the, e.g., photoreceptor layer 54, embedded therewithin. Thus, different tubular diameters may be used depending upon the recipient and the size of the implant.

Figure 25:
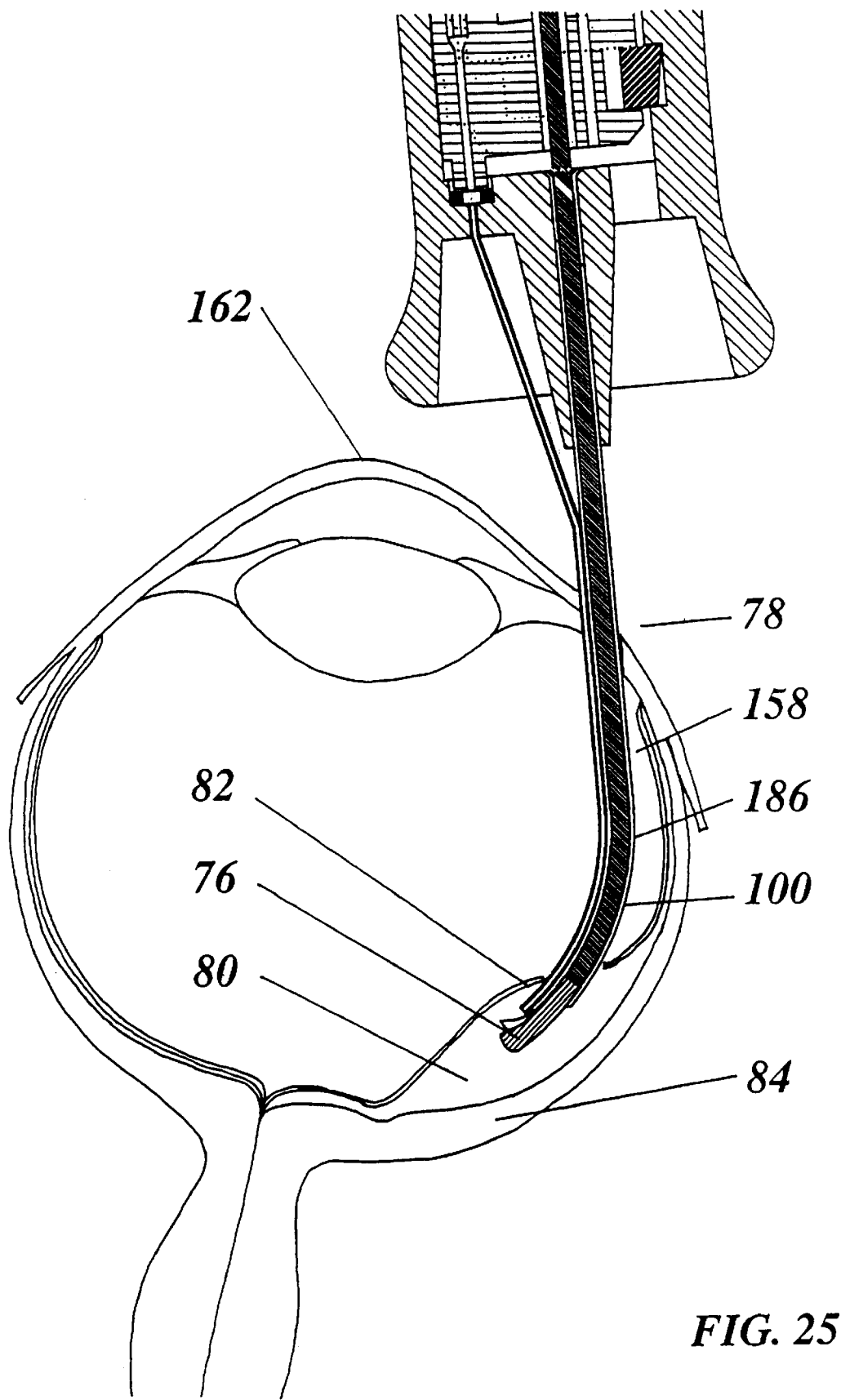
FIG. 25 is a horizontal section through an eye illustrating a pars plana surgical approach with the instrument cannula inserted into a bleb and illustrating a volute partially expressed into the subretinal space from the cannula.

As shown in FIG. 17, in a preferred embodiment, the edge 218 of the narrow tubular tip 212 of the delivery cannula 210 can be beveled to facilitate both the insertion of the instrument into the eye and the advancement of the tubular tip 212 into the subretinal area of the eye with a minimum of trauma. Further, as shown in FIG. 25, the beveled edge 218 of the tubular tip 212 facilitates gradual uncoiling of the graft 74 as one end of the graft is being ejected from the tubular tip. The edge 218 of the tubular tip 212 is preferably beveled at about 45 degrees, from the top to the bottom. For use in retinal surgery the narrow tubular tip 212 of the delivery cannula 210 is preferably curved along its longitudinal axis from the edge 218 of the tubular tip to the main body of the delivery cannula 210 as generally indicated at 220. The curvature 220 of the tubular tip 212 facilitates the manipulation of the instrument within the eye; particularly the manipulation of the instrument to a position between the retina and the supporting tissue 84 on the curved walls of the eye. The radius of curvature 220 of the tubular tip 212 will depend upon the procedure and the radius of curvature of the host eye. The narrow tubular tip 212 which is inserted into an incision made in an eye—the eye port—must be long enough to extend into the eye to reach in between the retina and the supporting sub-retinal tissue. Different lengths may be used for the narrow tubular tip 212 depending on the procedure employed and upon the recipient.

Figure 18A:
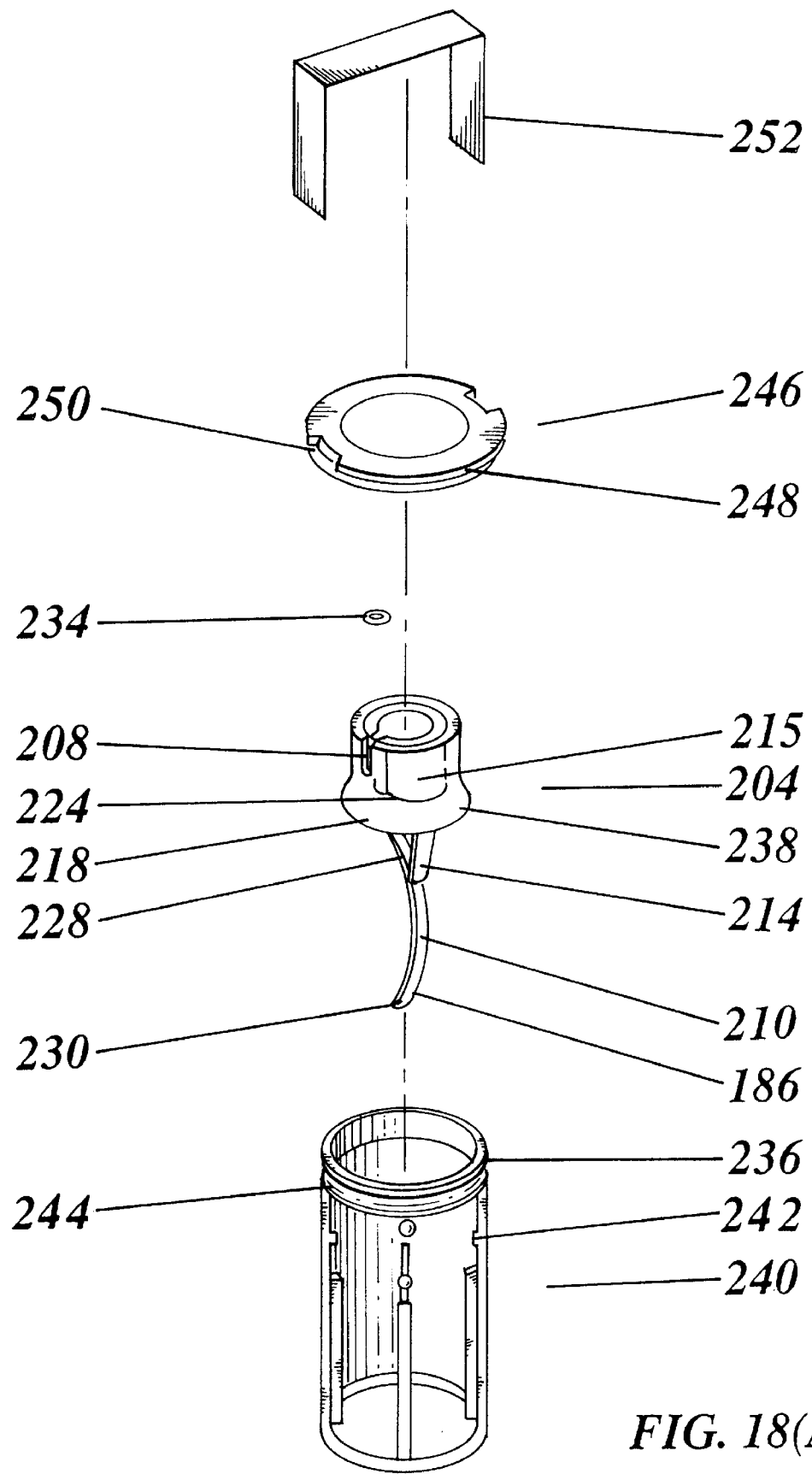
FIG. 18(A) is an exploded perspective view of the delivery cannula fitting with storage/transport container attached.
Figure 18B:
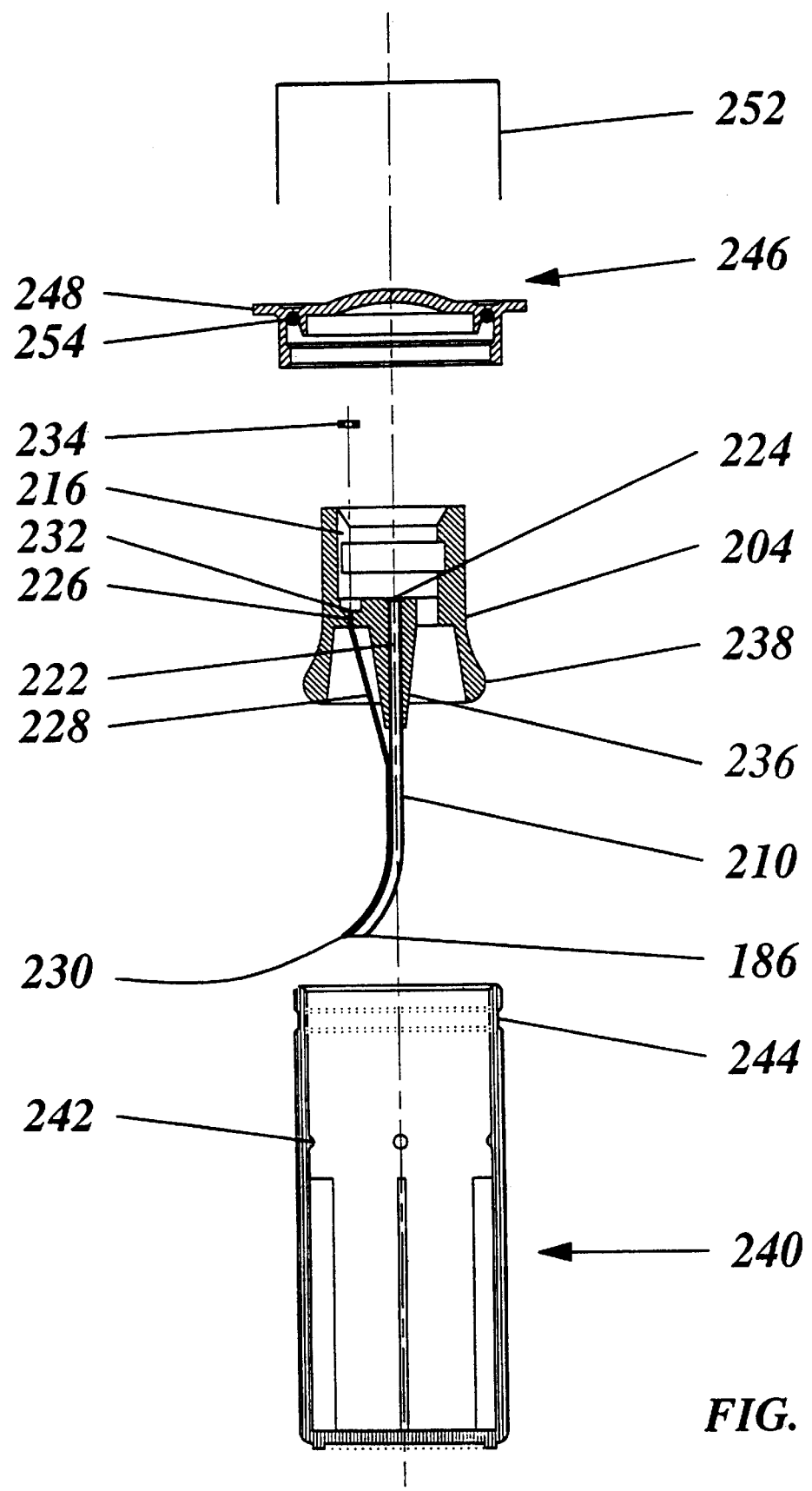
FIG. 18(B) is an exploded sectional view of the delivery cannula fitting with storage/transport container attached.
Figure 23:
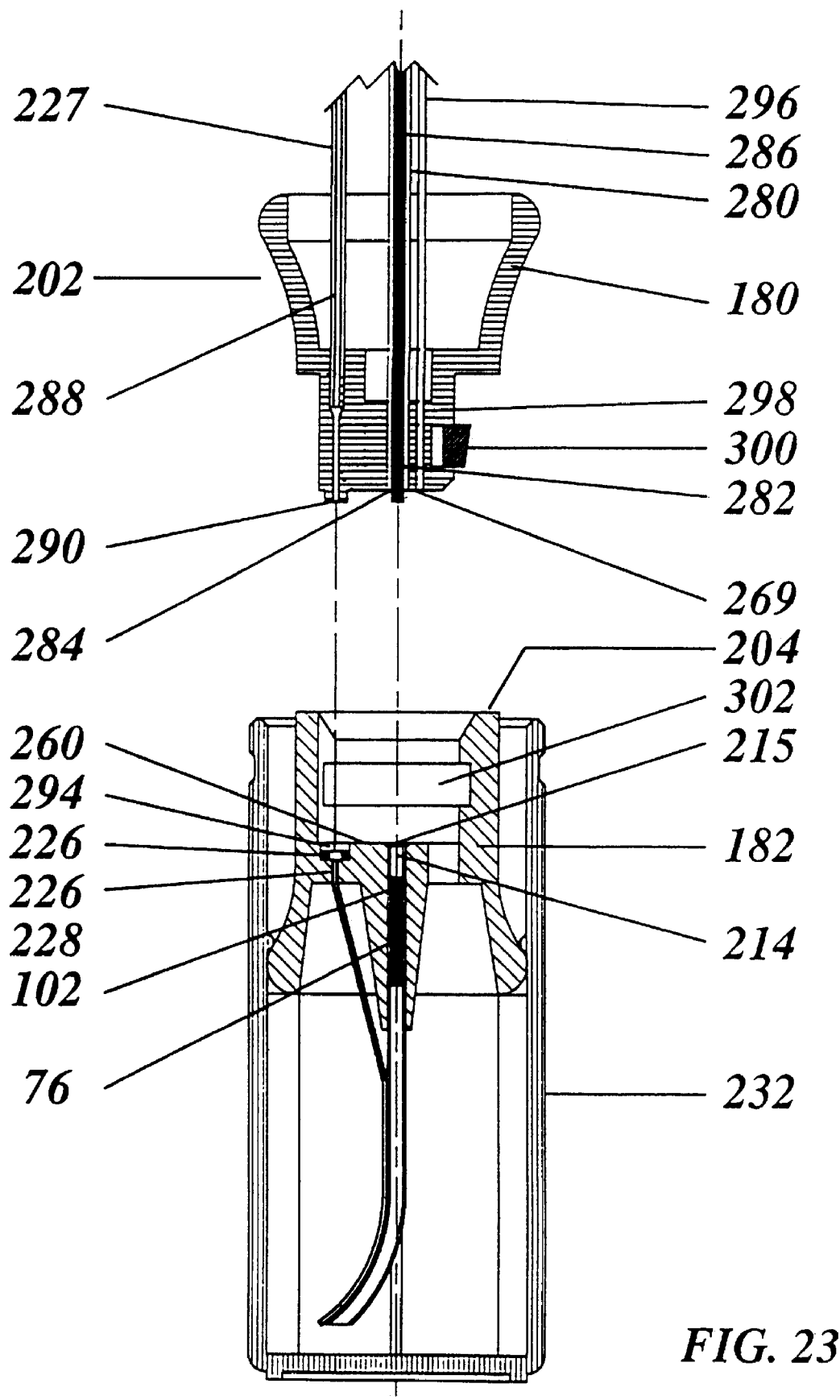
FIG. 23 is an exploded sectional view of the surgical instrument with a carrier in the attached delivery cannula.
Figure 24:
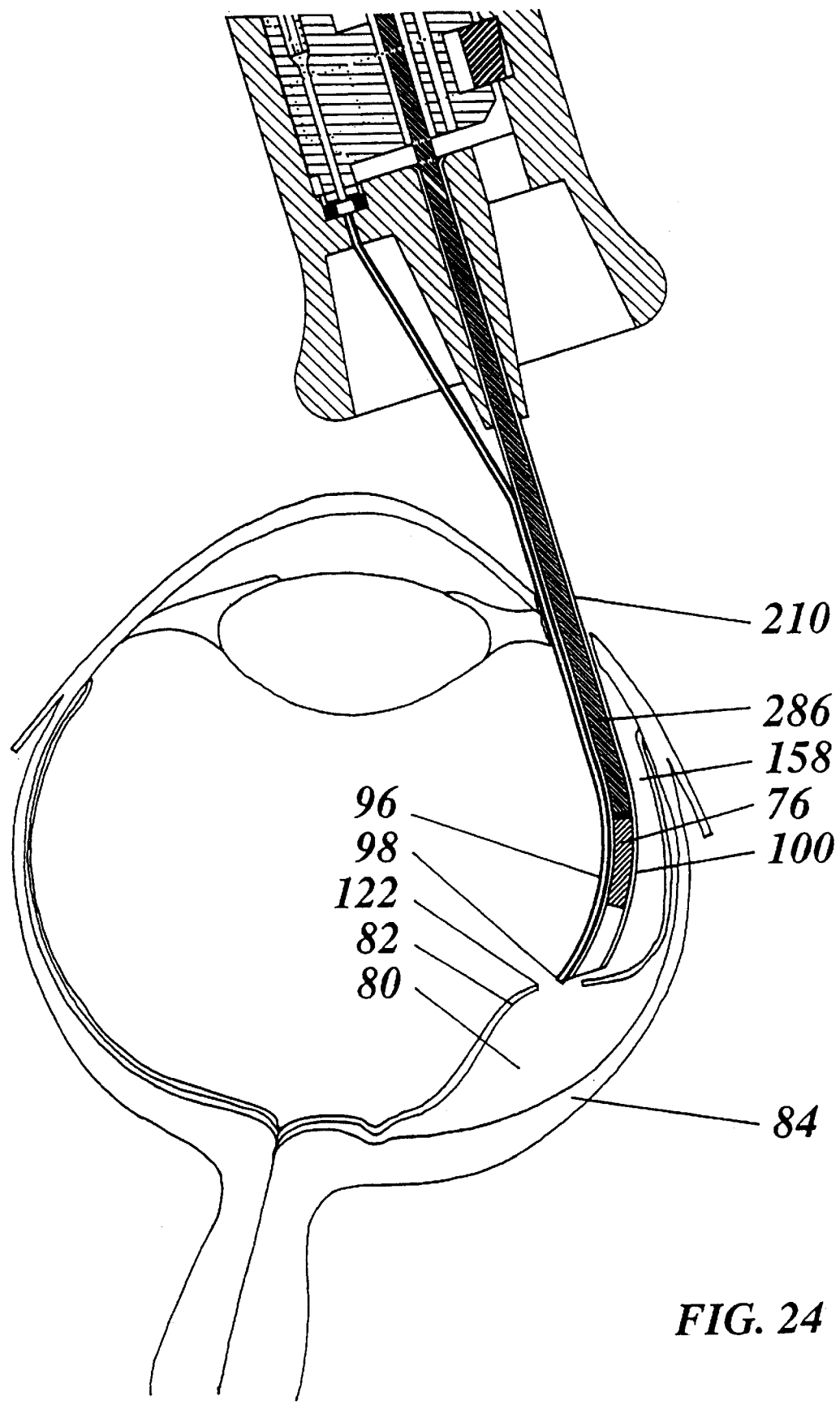
FIG. 24 is a horizontal section through an eye illustrating a pars plana surgical approach with the instrument cannula containing a volute extending partially across the eye.

Referring now to FIGS. 18(A) and 18(B), the delivery cannula 210 is mounted within the fitting 204. the fitting 204 is made of clear plastic and includes a central bore 222 adapted to receive the delivery cannula 210, the delivery cannula being held in place by an adhesive. The bore 222 has an opening 224 which is aligned with an opening in the male section 202 of the handpiece 200 when the two sections are in locking engagement as will be described later. An additional bore 226 is adapted for connection to an infusion conduit 227 FIG. 23 which can be attached to a source of fluid under pressure and will supply infusion fluid to infusion lumen 228. The infusion lumen 228 is used to supply a source of infusion fluid to the host eye during implantation of an implant such as graft 76 (FIGS. 23–25). The infusion lumen 228 is held in place in bore 226 by an adhesive and includes an opening 230 at the tubular tip 212 of the delivery cannula 210. Infusion bore 226 has an opening having an annular recess 232 for receiving O-ring gasket 234. O-ring gasket 234 acts to seal the connection between the lumen 228 and the infusion conduit 227.

The lumen 228 also allows for the aspiration of material from the tip 212 of the delivery cannula 210. The distal end of the lumen 228 can alternatively be connected to a source of suction so as to remove excess fluid and debris.

The opening 230 of lumen 228 is generally adjacent the tip 212 of the delivery cannula 210, and preferably slightly advanced relative to the tip 212. Thus, the lumen 228 can eject a stream of fluid from its opening 230 to a space ahead of the delivery cannula 210. The tip 212 of the delivery cannula 210 follows generally in the path opened by the fluid thus minimizing direct contact of the instrument and the eye tissue. The opening 230 of the lumen 228 may be beveled to facilitate the advancement of the delivery cannula 210, particularly at times when fluid is not being ejected from the lumen. The opening 230 is preferably beveled at about 45 degrees. The fluid ejected from the lumen 228 may be a saline solution, or some other fluid that will not harm the delicate eye tissues. Various substances, such as anti-oxidants, anti-inflammatories, anti-mitotic agents and local anesthetics can be provided in the fluid for treatment of the eye or implanted tissue.

The instrument can further include a pair of lead wires (not shown) terminating in an electrode at their distal ends. The electrode allows for cauterization of blood vessels. The proximal ends of the leads can be connected to a source of electrical power to seal broken blood vessels. It is possible to incorporate the leads onto the exterior wall of the delivery cannula 210.

The main body of the fitting 204 is substantially cylindrical and includes a central frusto-conical downwardly extending bottom portion 214 which provides additional support for the delivery cannula 210. An integrally formed annular rib 238 is provided on the main body to allow for locking engagement within the cannula carrier 240 container via bosses or projections 242. The cannula carrier container 240, which may be made of clear plastic, holds the delivery cannula 210 from the time of manufacturing through tissue loading, storage, and transportation, and does not have to be removed until the graft 74 is to be implanted.

Cannula carrier container 240 has an annular recess 244 on the exterior wall for sealing engagement with an internal rib formed in cap 246. Alternatively, the cannula carrier container 240 and the cap 246 can be threaded. The cap 246, which is flexible, also includes a lip 248 formed about the perimeter to facilitate lifting and removal. Notches 250 formed in cap 246 accept frangible label or seal 252 which may have information imprinted thereon such as expiration date, batch number, bar code, etc. A flexible gasket 254 provides a seal between the cap 246 and the carrier container 240.

Figure 19:
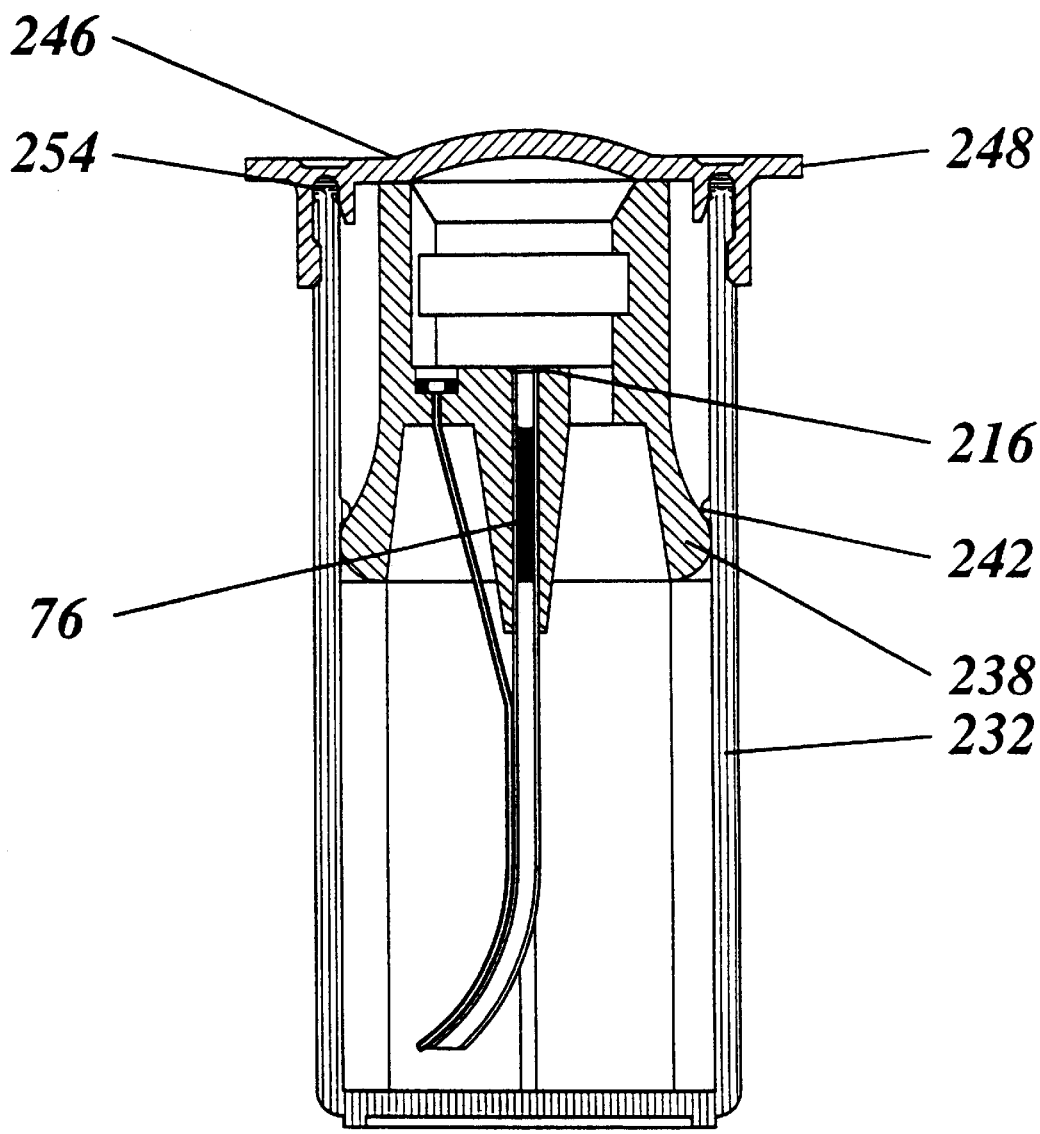
FIG. 19 is a cross-section of a loaded delivery cannula sealed in the storage transport of the present invention.

The entire assembly fits together to provide an airtight, watertight, transparent container for a loaded delivery cannula 210 as seen in FIG. 19. The sealed container can be used for transportation of a volute 76 with a minimal risk of damage or contamination. All components of the assembly except the cap 246 and seal 252 are transparent in a preferred embodiment. Of course, all components are sanitized or sterilized to reduce the possibility of infection during the procedure.

Figure 20:
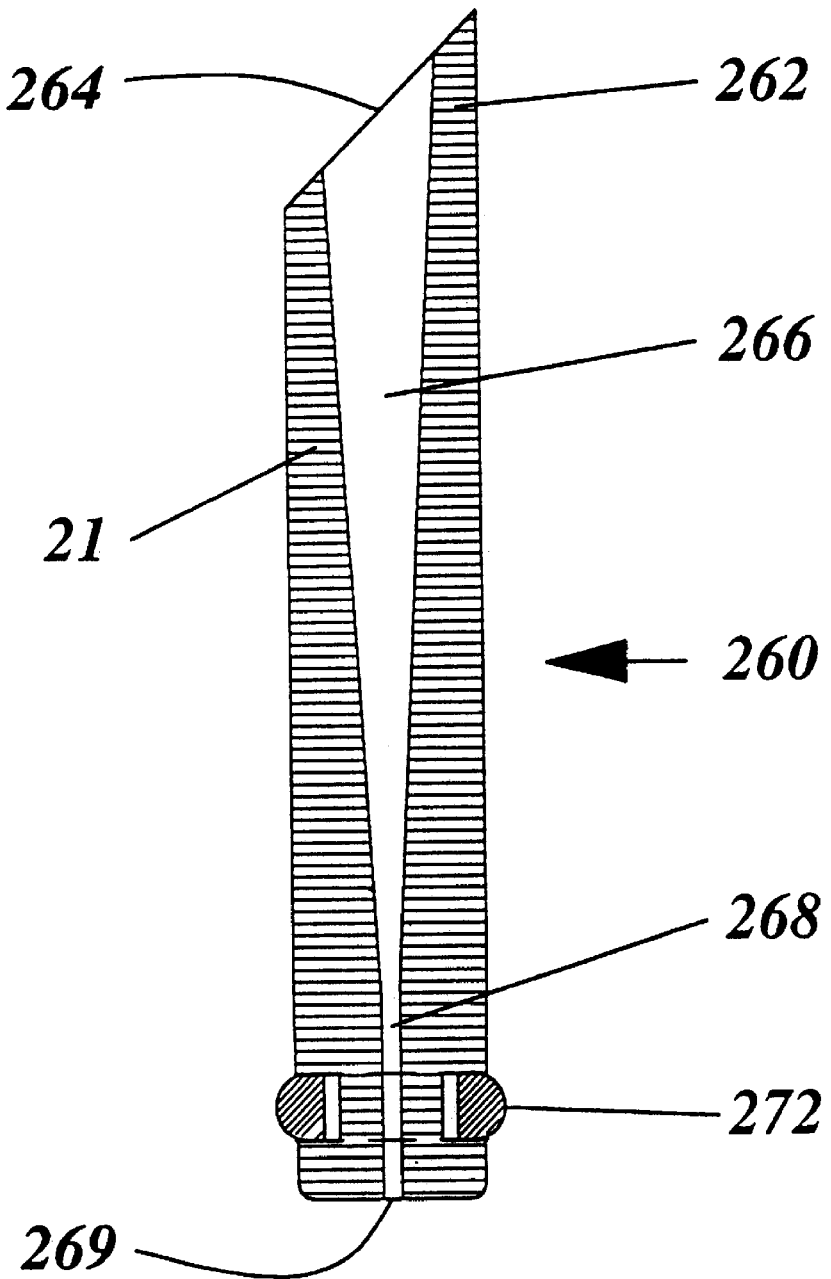
FIG. 20 is a sectional view of the loading cannula which is used for loading the graft into the delivery cannula.

Referring now to FIG. 20 a loading cannula 260 is shown. The loading cannula 260 is used to coil the planar structure 74 into a volute 76 for loading into the delivery cannula 210. The loading cannula 260 has a tubular top end portion 262 having an opening 264 for receiving the planar structure 74. The loading cannula 260 has an interiorly disposed funnel shaped bore 266 which terminates in a tubular bottom end portion 268 which has an opening 269 of smaller diameter than opening 264.

Figure 21:
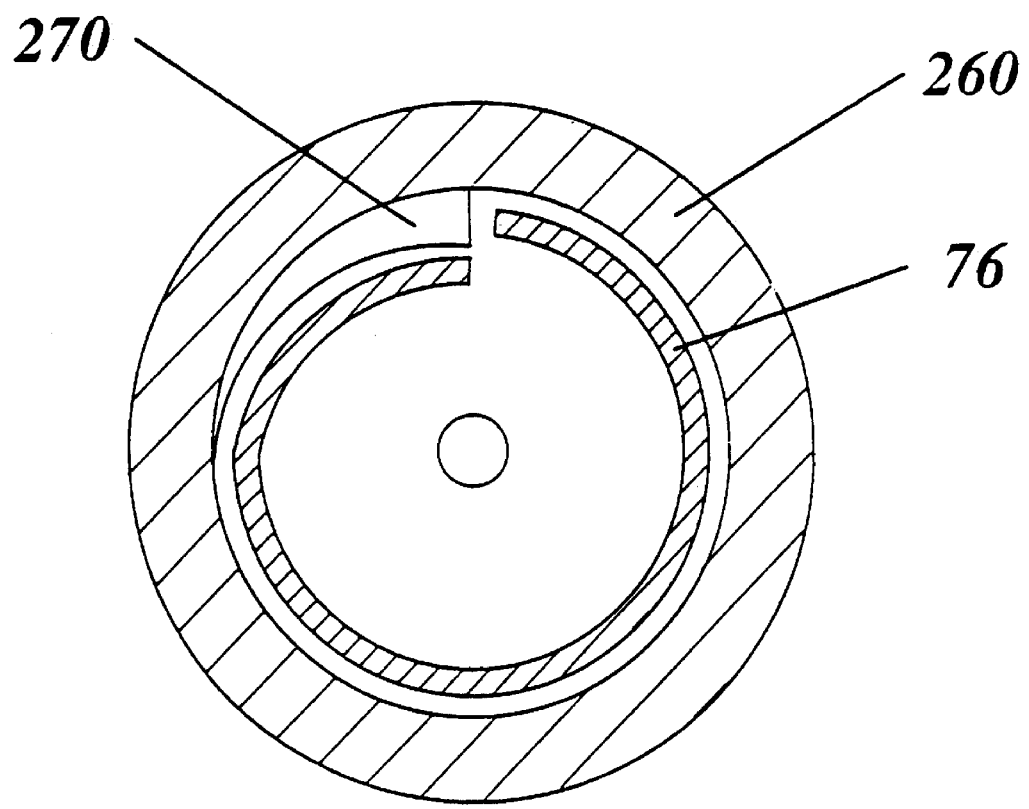
FIG. 21 is a horizontal section taken along line 21—21 of FIG. 20 illustrating a ramp within the loading canula.

In an alternative embodiment the loading cannula 260 may include a ramp 270 (FIG. 21) formed on the interior surface at the transition from the top end portion 262 to the funnel bore 266. The ramp 270 directs one side of a planar sheet underneath the other side of the graft 74 to form the volute 76. In this embodiment of the loading cannula 260, the side edges 72 of the carrier sheet 70 can be cut vertically, instead of skived to form a graft 74. The ramp 270 prevents buckling of the graft 74 by not permitting the side edges to contact each other, and can act to align the volute 76 in a specific orientation (e.g. one edge of the volute can be maintained in a particular orientation).

As shown and described herein, the inner diameter of the top end portion 262 of the loading cannula 260 is approximately 5 millimeters. The inner diameter of the bottom end portion 268 is 0.043 inches to match the inner diameter of the delivery cannula 210. The inner surface of the loading cannula 260 has a gradual slope which allows for controlled coiling of the graft 74. The slope of the funnel 266 cannot be too abrupt as to cause the graft 74 to buckle. It should be noted that the actual measurements will change depending on the size of the graft or implant and the recipient.

As is the case with the delivery cannula 210, the loading cannula 260 can be made of acrylic, glass, or some other material that is sterilizable and transparent.

Figure 22:
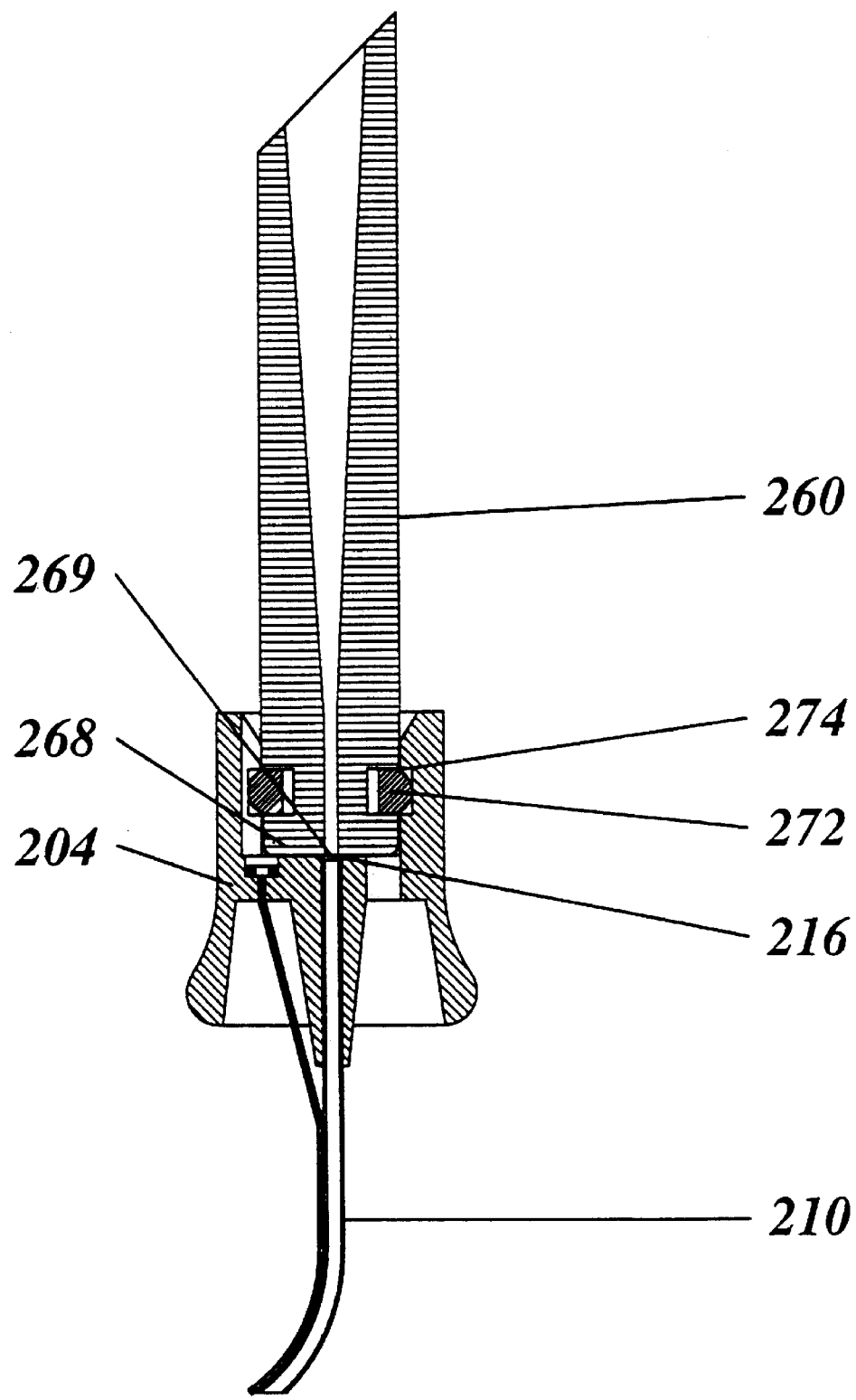
FIG. 22 is a sectional view of the relative positions of the loading canula and the delivery cannula during tissue transfer.

The bottom end 268 of the loading cannula 260 can be placed inside of the fitting 204 so that the bottom end opening 269 is axially aligned with the flared opening 216 of the delivery cannula 210 as shown in FIG. 22. This arrangement allows for formation of the volute 76, and for loading of the volute 76 into the delivery cannula 210. It can be seen that the loading cannula 260 includes an annular ring 272 to allow for stable nesting during tissue transfer. The ring 272 is made of compressible material and engages annular recess 274 in the fitting 204 (FIG. 19) to stabilize the loading cannula 260 relative to the delivery cannula 210 during tissue transfer. Thus, the flared end 216 of the delivery cannula 210 is aligned with the bottom end opening 269 of the loading cannula 260 thereby providing a smooth, constant diameter inner surface. The transition from the interior surface of the loading cannula 260 to the interior surface of the delivery cannula 210 is made as smooth as possible to avoid stress on the volute 74.

Referring now to FIG. 23 an exploded sectional view of the handpiece 200, and cannula carrier container 240 are shown. The male section 202 of the handpiece 200 includes three axial bores. A conduit 280 is secured in bore 282, the conduit 280 having a distal end terminating at an orifice 284. A plunger 286 can be coaxially mounted within the conduit 280 for expressing the volute 76 or other material in cannula 210, the proximal end of the plunger 286 preferably being connected to a source of motive power such as a microprocessor controlled stepper motor assembly as described in our copending U.S. Patent application Ser. No. 08/395,701 entitled, "MEDICAL LINEAR ACTUATOR FOR SURGICAL DELIVERY, MANIPULATION, AND EXTRACTION AND ASSOCIATED METHODS", filed on even date herewith which is herein incorporated by reference. Alternatively, the proximal end of the conduit 280 can be connected to a source of fluid pressure.

The infusion conduit 227 is connected into bore 288 and secured in place by an adhesive. It can be seen that the bore 288 is flared to reduce turbulence caused by the narrowing of the bore 288. The bore 288 is narrowed so that its inner diameter matches the inner diameters of the infusion conduit 227 and the infusion lumen 228. A collar 290 projecting from the bottom surface 292 of the male section 202 of the handpiece 200 extends into a recess 294 of the fitting 204 when the male section 202 and the fitting 204 are connected thereby providing for axial alignment of the infusion conduit 227, bore 288, bore 226, and the top end of the infusion lumen 228. Thus, a constant diameter inner surface is provided for infusion fluid flow.

A fiber optic filament 296 is secured in the third bore 298 and connected to a light source (not shown). The fiber optic cable 296 serves to provide illumination to facilitate precise positioning of the delivery cannula 210 within the eye and the proper placement of the graft 74. Alternatively, the fiber optic filament 296 could extend to the tip of the delivery cannula 210 and a lens could be provided at the proximal end of the fiber optic element 296 so that the filament can be used for direct observation at the tip 212 of the delivery cannula. Additionally, the fiber optic filament 296 could allow for laser-light cautery to control subretinal bleeding.

Thus the handpiece 200 is connectable to a source of infusion/aspiration, a source of motive power for expressing/retracting the volute 76, and a source of illumination.

The male section 202 can be attached to delivery cannula fitting 204 while the cannula carrier container 240, with loaded cannula 210, is attached to fitting 204. The fitting 204 is inserted into the carrier 240 until the pieces lock together. Locking of the male section 202 to the cannula fitting 204 is accomplished by engagement of a compressible locking member 300 with an annular recess 302 formed within the cannula fitting. After the male section 202 is locked to the fitting 204 the cannula carrier 240 can be removed. Thus, a delivery cannula 210 loaded with a volute 76, and ready for the implantation procedure is provided. It should be noted that in a preferred embodiment, the loading cannula 260, the delivery cannula 210, and the delivery cannula fitting 204 are all transparent to allow for viewing of the graft 74 through the entire procedure from loading until implantation.

As shown in FIG. 23, the plunger 286 is preferably a thin cable received in the delivery cannula 210 so that relative advancement of the plunger through the delivery cannula main body and into the tubular tip 212 with respect to the main body urges the coiled cellular structure 76 through the main body and into and out of tip 212 of the delivery cannula 210. To reduce the possibility of damage to the fragile cellular structure 76 caused by direct contact between the plunger 286 and the volute, the coiled cell containing structure is protected from direct contact with the plunger 286 by a spacer made from a flexible material which is inserted into the delivery cannula 210 prior to the insertion of the plunger. The spacer is guided to lay on top of the coiled cellular structure 76 and thereby protects the coil (volute) from direct contact with the mechanical plunger 286. A flexible but not substantially compressible gelatinous material can be used for the spacer. The plunger 286 projects a sufficient distance from the open end 214 so that the projecting end of the plunger 286 can be manipulated even when the tubular tip 212 of the instrument 178 is in the eye.

With reference to FIG. 24, a preferred method of operating the instrument comprises first placing tip 212 with the volute 76 therein within the subretinal area 80 of an eye, the plunger 286 is manipulated to eject the coiled cellular structure 76 from tip 212 of the instrument. While the plunger 286 provides the greatest control over the ejection of the volute 76 into the eye, some caution must be exercised while operating the plunger because of the increased likelihood of damage to the volute 76.

Alternatively, the plunger means may comprise means for applying fluid pressure (not shown) on the contents of the delivery cannula 210. In this case, the flared opening 216 for the delivery cannula 210 is connected to a source of fluid under pressure. Fluid can be selectively supplied to the delivery cannula 210 to displace its contents. The fluid may be viscous, for example 2% carboxymethylcellulose, or non-viscous. Particularly in the later case, it may be desirable to have gelfoam or some other relatively soft spacer material in the tube to act as a mechanical plunger and to separate the fluid from the cell structure being implanted. As previously discussed, gelatin is satisfactory to protect a volute or other implant because it is semi-solid and will dissolve harmlessly if it is ejected from the instrument. While the use of fluid pressure as the plunger means significantly decreases the likelihood of damage to the volute 76, it also results in a significant reduction in the degree of control over the ejection of the volute 76 from the delivery cannula 210.

Of course, two or more of the features described with respect to the alternate embodiments could be combined, as necessitated by the particular circumstances.

The method of transplanting a volute 76 into the subretinal area of an eye comprises assembling a transplantable material such as retinal pigment epithelial tissue, choroidal tissue, Bruch's membrane and/or retinal cells 54 into a graft 74 as previously described. It will be understood that the transplantable material may be formed into a graft without the gelatin carrier sheet and still be within the scope of the present invention. Preferably, however, the graft is assembled with a carrier sheet 70. The transplantation method provides for the graft 74 to be loaded into the delivery cannula 210 by first nesting loading cannula 260 into the delivery cannula fitting 204 by pushing the bottom end 269 of the loading cannula into the delivery cannula fitting 204 until compressible annular ring 272 is seated entirely within recess 274 as shown in FIG. 22. The graft 74 is placed, one end first, in the opening at the top end portion 262 of the loading cannula 260 so that the carrier 70 will be coiled with the outer segment of the photoreceptor layer 54 facing toward the outside of the convolutions 77 of the resultant volute 76 and so that the volute will uncoil in said subretinal area 80 with the outer segment of the photoreceptorlayer facing toward the pigment epithelial layer 84 of the host eye. The loading cannula 260 is then filled with viscoelastic fluid which facilitates the graft's progression into the tapered passage or funnel 266. The graft 74 slidably proceeds into the funnel 266 engaging the progressively narrowing tapered surface causing the graft to progressively coil. As the interior walls of the funnel bore 266 narrow sufficiently to cause the sides 72 of the carrier sheet 70 to make contact, one side 72 of the sheet 70 slides underneath the other side of the carrier sheet due in part, to the carrier's skived sides. The skived sides 72 prevent any buckling of the carrier sheet 70 as the side edges make contact. In the alternative embodiment shown in FIG. 21, as the interior walls of the loading cannula 260 narrow sufficiently to cause the sides 72 of the graft 74 to be in proximity to each other, ramp 270 directs one side underneath the opposite side of the planar sheet to begin coiling to form the volute 76. At some point in the funnel 266 the convolutions 77 of the coil 76 are sufficiently constricted so that the viscoelastic fluid 120 can no longer force the coil through the funnel. A gelfoam spacer 102 is placed on top of the coil 76, a bulb (not shown) is placed on the open end of the loading cannula 260 to create a vacuum so that the fluid 120 and the volute 76 remain in the loading cannula 260 and the delivery cannula 210. A syringe can be inserted through the bulb to inject more fluid 120 as required. The plunger 286 is inserted into the open end of the loading cannula 260 and manipulated to be in contact with the gelfoam spacer 102. The plunger 286 is carefully advanced to force the graft 74 through the funnel 266 to further coil the graft into a volute 76 and into and through the curved path 220 of the tubular tip 212.

The host eye is prepared so as to reduce bleeding and surgical trauma. A scleral pars plana surgical approach to the subretinal space is preferred (FIG. 25), but other approaches, such as transcorneal and trans-scleral, may be used. A small incision (about 0.75 mm–2.0 mm) is made in the pars plana of an eye large enough to insert delivery cannula 210. Following vitrectomy, the eye can be cooled by infusion of cooled balanced salt solution through a second pars plana incision into the vitreal cavity of the eye to avoid dissolution of the carrier sheet 70 of the volute 76 during the surgical procedure. A portion of the retina 82 at the site of implantation is raised away from the pigment epithelial cell lining 84 by making an incision 122 in the retina and infusing balanced salt or another suitable solution in the subretinal area to form a bleb 80 at the implantation site under the retina 82. The retina 82 may be detached by the gentle force of a perfusate such as a saline-like fluid, carboxymethylcellulose, or 1–2% hyaluronic acid ejected from the lumen 228 to create a bleb 80. Advantageously, the fluid may additionally contain anti-oxidants, anti-inflammation agents, anesthetics or agents that slow the metabolic demand of the host retina 82. The delivery cannula 210 with the volute 76 at its tubular tip 212 is inserted through the pars plana port, through the vitreal cavity and into the subretinal space. As illustrated in FIG. 24, the delivery cannula 210 is then manipulated so that the edge 218 of the tubular tip 212 is in line with the incision 122 of the bleb 80. The entire tip 212 of the instrument 178 is inserted through the retinotomy into the bleb 80 and the volute 76 is ejected by carefully advancing the plunger as shown in FIG. 25. The volute 76 is ejected from the beveled edge 218 of the tubular tip 212 and uncoils under its inherent uncoiling memory as it is ejected from the bevelled edge so that the outer segments of photoreceptor layer 54 is facing the pigment epithelial layer 84. If the volute 76 does not uncoil entirely, micro picks can be used to completely uncoil the graft 74.

The bleb 80 is then deflated by evacuation of fluid within the bleb or by tamponade so that the graft 74 is held in a sandwich-like arrangement at the desired position between the retina 82 and pigment epithelial cell lining 84. The incision 122 in the bleb 80 may be closed cauterly. The gelatin carrier sheet 70 dissolves when it reaches normal body temperature. The edges of the scleral incision are abutted after removal of the forceps and sutured using standard opthalmological procedures.

As shown and described in parent application Ser. No. 07/566,996, a trans-choroidal, scleral and corneal surgical approach may be used as an alternative to the pars plana approach described above. Except for. the point of entry, the surgical technique is essentially the same as outlined above.

In view of the above, it will be seen that the several objects of the invention are achieved and other advantages attained.

As various changes could be made in the above surgical instruments, compositions of matter and methods without departing from the scope of the invention, it is intended that all matter contained in the above description or shown in the accompanying drawings shall be interpreted as illustrative and not in a limiting sense.

What is claimed is:

1. An instrument for the implantation of an implant in a host, comprising:

a tubular body, and a first housing, said tubular body having a first end for receiving an implant and a second end for insertion in a host, said tubular body having a first conduit passing from said first end to said second end, wherein said tubular body is connected to said first housing, said first housing having a first end and a second end, said instrument further comprising: plunger means for expressing an implant contained within the instrument, said plunger means being at least partially contained within a second housing, and first means on said first housing for engagement with a storage container within which said tubular body and housing may be sealed, and second means on said first housing for locking engagement with said second housing wherein, when said first housing is in locking engagement with said second housing, said conduit in said first tubular body is aligned with said plunger means to permit said plunger means to extend into said conduit to provide expression of an implant contained within said tubular body by said plunger means, and at least one of said housings forms a handpiece for manipulation of said tubular body, wherein said plunger means comprises a cable member capable of relative movement inside of said conduit in said tubular body, the instrument also including electromechanical actuation means for advancing and retracting said cable member inside of said conduit.

2. The instrument of claim 1, further including a container for said tubular body and said first housing, said container having an interior cavity into which said tubular body may be completely inserted, said interior cavity having surfaces, said container further having positioning means for engagement with said first means on said first housing for positioning said tubular body and said first housing in said container, wherein, when said tubular body is located within said interior of said container and said first means on said first housing is operably engaged with said positioning means, said tubular body will not contact said surfaces of said container, whereby an implant may be placed in said tubular body, and the instrument containing the implant sealed in said container with said first means on said first housing operably engaged with said positioning means, so that the implant and said tubular body will be protected in said container during storage and shipping.

3. The instrument of claim 2, wherein said second end of said tubular body may be inserted into the eye of a host to permit expression of an implant contained within said tubular body into the host eye.

4. The instrument of claim 3, wherein said second end of said tubular body may be inserted beneath the retina of a host eye to permit expression of said implant beneath the retina the host eye.

5. The instrument of claim 4, wherein said implant is a coiled planar implant, which, upon expression beneath the retina of a host eye, will at least partially uncoil.

6. The instrument of claim 2, further comprising an implant located within said tubular body, said implant comprising a substance selected from the group comprised of photoreceptor cells, retinal pigment epithelial cells, and drugs.

7. A kit for storing and transporting an implant loaded in an implanting instrument, comprising:

a container, an instrument within said container, and an implant within said instrument, wherein:

said instrument comprises a tubular body, and a first housing, said tubular body has a first end for receiving an implant and a second end for insertion in a host, and a first conduit passing from said first end to said second end, wherein said tubular body is connected to said first housing, and said implant is located within said tubular body, said first housing has first means for engagement with said container, said container having surfaces which form an interior cavity into which said tubular body may be completely inserted, said container further having positioning means for engagement with said first means on said first housing for positioning said tubular body and said first housing in said container, wherein, when said tubular body is located within said interior cavity of said container and said first means on said first housing is operably engaged with said positioning means, said tubular body will not contact said surfaces of said container, said implant comprises a substance selected from the group comprised of photoreceptor cells, retinal pigment epithelial cells, and drugs, and said first housing further comprises second means thereon for locking engagement with a second housing, whereby, when said second housing contains plunger means for expression of an implant contained within said tubular body and said first housing is in locking engagement the second housing, the plunger means can extend into said conduit in said tubular body to provide expression of an implant contained in said tubular body.

8. The instrument of claim 7, wherein said second end of said tubular body may be inserted beneath the retina of a host eye to permit expression of said implant beneath the retina the host eye.

9. The instrument of claim 8, wherein said implant is a coiled planar implant, which, upon expression beneath the retina of a host eye, will at least partially uncoil.

\* \* \* \* \*